United States Patent
Strominger et al.

(10) Patent No.: US 7,456,252 B2
(45) Date of Patent: *Nov. 25, 2008

(54) THERAPEUTIC PEPTIDES FOR DEMYELINATING CONDITIONS

(75) Inventors: Jack L. Strominger, Lexington, MA (US); Masha Fridkis-Hareli, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 362 days.

This patent is subject to a terminal disclaimer.

(21) Appl. No.: 11/150,755

(22) Filed: Jun. 10, 2005

(65) Prior Publication Data

US 2006/0020109 A1 Jan. 26, 2006

Related U.S. Application Data

(63) Continuation of application No. 10/056,583, filed on Jan. 24, 2002, now Pat. No. 6,930,168.

(60) Provisional application No. 60/263,569, filed on Jan. 24, 2001.

(51) Int. Cl.
*C07K 2/00* (2006.01)
*C07K 7/08* (2006.01)
*A61K 38/10* (2006.01)
*A61K 38/16* (2006.01)

(52) U.S. Cl. .................. 530/326; 530/300; 435/810; 435/975; 514/13; 514/14

(58) Field of Classification Search ................. None
See application file for complete search history.

(56) References Cited

U.S. PATENT DOCUMENTS

| | | | | |
|---|---|---|---|---|
| 5,614,192 A | * | 3/1997 | Vandenbark | 424/185.1 |
| 5,827,516 A | * | 10/1998 | Urban et al. | 424/93.21 |
| 5,880,103 A | * | 3/1999 | Urban et al. | 514/44 |
| 6,509,033 B1 | * | 1/2003 | Urban et al. | 424/450 |
| 2003/0103993 A1 | * | 6/2003 | Deshpande et al. | 424/185.1 |
| 2004/0038887 A1 | * | 2/2004 | Strominger et al. | 514/12 |

FOREIGN PATENT DOCUMENTS

WO WO 94/04171 A1 * 3/1994
WO WO 02/057291 A2 * 7/2002

OTHER PUBLICATIONS

Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Fridkis-Hareli et al. Novel synthetic amino acid copolymers that inhibit autoantigen-specific T cell responses and suppress experimental autoimmune encephalomyelitis. J Clin Invest 109(12): 1635-1643, 2002.*
Stern et al. Peptide 15-mers of defined sequence that substitute for random amino acid copolymers in amelioration of experimental autoimmune encephalomyelitis. Proc Natl Acad Sci USA 102(5): 1620-1625, 2005.*
Fridkis-Hareli et al. Binding of random copolymers of three amino acids to class II MHC molecules. Int Immunol. 11(5):635-641, 1999.*
Fridkis-Hareli et al. 2001 Synthetic peptides that inhibit binding of the myelin basic protein 85-99 epitope to multiple sclerosis-associated HLA-DR2 molecules and MBP-specific T-cell responses. Hum Immunol 62(8): 753-763, 2001.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*

* cited by examiner

*Primary Examiner*—Bridget E Bunner
(74) *Attorney, Agent, or Firm*—Sonia K. Guterman; Lawson & Weitzen, LLP

(57) ABSTRACT

The invention provides peptide compositions and methods of making and using therapeutic compositions comprising peptides for the treatment of a subject having a demyelinating condition.

4 Claims, 8 Drawing Sheets

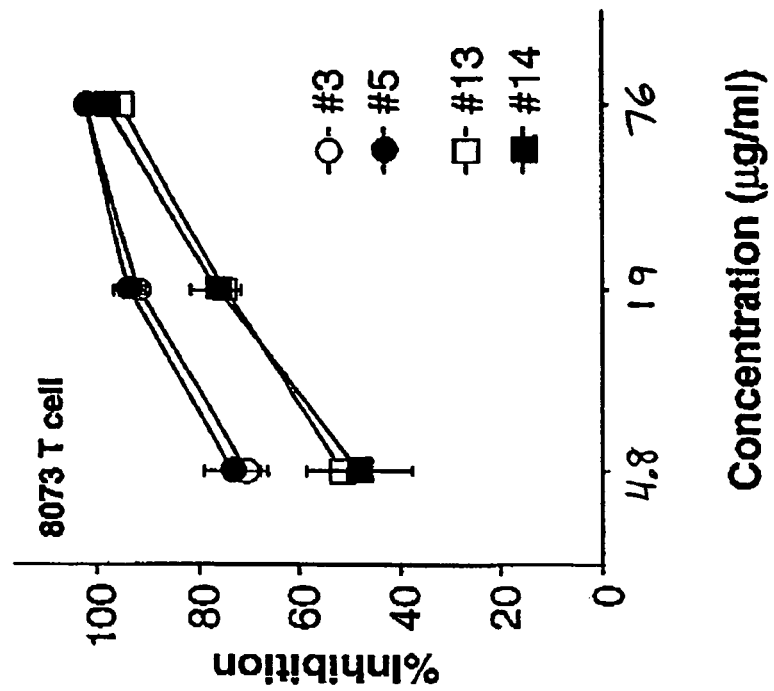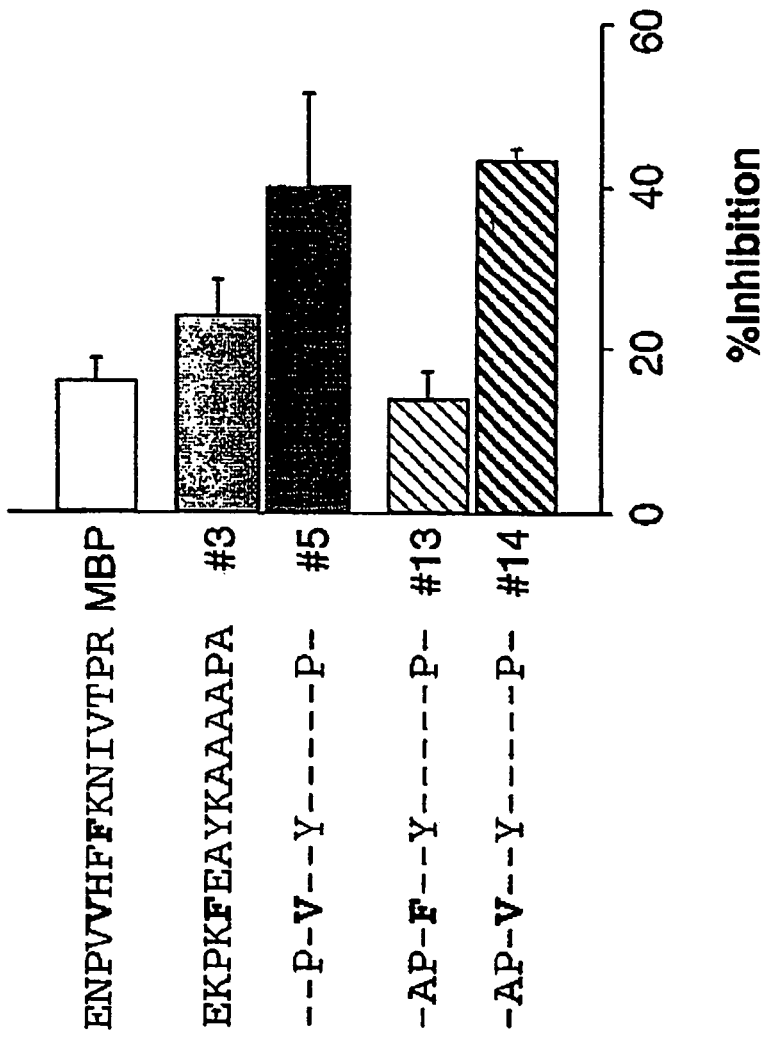

SEQUENCE LISTING

<160> NUMBER OF SEQ ID NOS: 99

<210> SEQ ID NO 1
<211> LENGTH: 15
<212> TYPE: PRT
<213> ORGANISM: Homo sapiens
<220> FEATURE:
<221> NAME/KEY: DOMAIN
<222> LOCATION: 85 - 99
<223> OTHER INFORMATION: Immunodominant peptide of MBP, recognized by
      HLA-DR2 haplotype

<400> SEQUENCE: 1

Glu Asn Pro Val Val His Phe Phe Lys Asn Ile Val Thr Pro Arg
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 2

Ala Lys Lys Glu Tyr Ala Ala Ala Ala Ala Ala Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 3

Ala Lys Glu Glu Tyr Ala Ala Ala Ala Ala Ala Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 4

Ala Lys Glu Ala Tyr Ala Ala Ala Ala Ala Ala Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 5

Ala Glu Lys Glu Tyr Ala Ala Ala Ala Ala Ala Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 6

Glu Lys Lys Ala Tyr Ala Ala Ala Ala Ala Ala Ala Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 7

Lys Glu Glu Tyr Ala Ala Ala Ala Ala Ala Ala Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 8

Ala Glu Lys Ala Tyr Ala Ala Ala Ala Ala Ala Ala Ala Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 9

Glu Lys Ala Ala Tyr Ala Ala Ala Ala Ala Ala Ala Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 10

Glu Glu Lys Ala Tyr Ala Ala Ala Ala Ala Ala Ala Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 11

Ala Lys Glu Ala Ala Ala Ala Tyr Ala Ala Ala Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: The peptide was designed and synthesized.

```
<400> SEQUENCE: 12

Glu Lys Glu Ala Ala Ala Ala Tyr Ala Ala Ala Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 13

Lys Glu Lys Ala Ala Ala Ala Tyr Ala Ala Ala Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 14

Ala Lys Ala Glu Ala Ala Ala Tyr Ala Ala Ala Ala Ala Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 15

Ala Glu Lys Ala Ala Ala Ala Tyr Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 16

Ala Lys Lys Ala Ala Glu Ala Tyr Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 17

Ala Lys Ala Ala Ala Ala Glu Tyr Ala Ala Ala Ala Ala Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 18
```

```
Ala Glu Lys Ala Tyr Ala Ala Tyr Ala Ala Ala Ala Ala Ala Ala
 1               5                  10                  15
```

<210> SEQ ID NO 19
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 19

```
Ala Glu Glu Ala Tyr Lys Ala Tyr Ala Ala Ala Ala Ala Ala Ala
 1               5                  10                  15
```

<210> SEQ ID NO 20
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 20

```
Ala Glu Lys Lys Tyr Ala Ala Tyr Ala Ala Ala Ala Ala Ala Ala
 1               5                  10                  15
```

<210> SEQ ID NO 21
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 21

```
Ala Ala Glu Lys Tyr Ala Ala Tyr Ala Ala Ala Ala Ala Ala Ala
 1               5                  10                  15
```

<210> SEQ ID NO 22
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 22

```
Ala Glu Glu Lys Tyr Ala Ala Tyr Ala Ala Ala Ala Ala Ala Ala
 1               5                  10                  15
```

<210> SEQ ID NO 23
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 23

```
Ala Lys Glu Ala Tyr Ala Ala Tyr Ala Ala Ala Ala Ala Ala Ala
 1               5                  10                  15
```

<210> SEQ ID NO 24
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 24

-continued

```
Ala Ala Lys Glu Tyr Ala Ala Tyr Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 25

Ala Lys Ala Glu Tyr Ala Ala Tyr Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 26

Ala Glu Ala Lys Tyr Ala Ala Tyr Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 27

Ala Ala Glu Glu Tyr Lys Ala Tyr Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 28

Ala Lys Glu Glu Tyr Ala Ala Tyr Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 29

Ala Lys Glu Lys Tyr Ala Ala Tyr Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 30

Ala Lys Ala Ala Tyr Glu Ala Tyr Ala Ala Ala Ala Ala Ala Ala
```

```
<210> SEQ ID NO 31
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 31

Ala Ala Lys Ala Tyr Glu Ala Tyr Ala Ala Ala Ala Ala Ala Ala
 1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 32

Ala Glu Ala Glu Tyr Lys Ala Tyr Ala Ala Ala Ala Ala Ala Ala
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 33

Ala Glu Ala Lys Tyr Glu Ala Tyr Ala Ala Ala Ala Ala Ala Ala
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 34

Ala Ala Lys Lys Tyr Glu Ala Tyr Ala Ala Ala Ala Ala Ala Ala
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 35

Ala Ala Glu Lys Tyr Glu Ala Tyr Ala Ala Ala Ala Ala Ala Ala
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 36

Ala Ala Ala Glu Tyr Lys Ala Tyr Ala Ala Ala Ala Ala Ala Ala
 1               5                  10                  15
```

<210> SEQ ID NO 37
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 37

Glu Ala Glu Lys Tyr Ala Ala Tyr Ala Ala Ala Ala Ala Ala Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 38

Glu Lys Ala Glu Tyr Ala Ala Tyr Ala Ala Ala Ala Ala Ala Ala
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 39

Glu Lys Glu Ala Tyr Ala Ala Tyr Ala Ala Ala Ala Ala Ala Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 40

Glu Ala Lys Glu Tyr Ala Ala Tyr Ala Ala Ala Ala Ala Ala Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 41

Glu Ala Lys Ala Tyr Ala Ala Tyr Ala Ala Ala Ala Ala Ala Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 42

Ala Ala Ala Glu Tyr Ala Ala Tyr Lys Ala Ala Ala Ala Ala Ala
1               5                   10                  15

```
<210> SEQ ID NO 43
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 43

Ala Ala Glu Lys Tyr Ala Ala Tyr Lys Ala Ala Ala Ala Ala Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 44

Ala Lys Glu Ala Tyr Ala Ala Tyr Lys Ala Ala Ala Ala Ala Ala
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 45

Ala Glu Ala Lys Tyr Ala Ala Tyr Lys Ala Ala Ala Ala Ala Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 46

Ala Glu Glu Ala Tyr Ala Ala Tyr Lys Ala Ala Ala Ala Ala Ala
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 47

Ala Lys Ala Glu Tyr Ala Ala Tyr Lys Ala Ala Ala Ala Ala Ala
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 48

Ala Lys Glu Glu Tyr Ala Ala Tyr Lys Ala Ala Ala Ala Ala Ala
1               5                   10                  15
```

-continued

```
<210> SEQ ID NO 49
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 49

Ala Glu Glu Lys Tyr Ala Ala Tyr Lys Ala Ala Ala Ala Ala Ala
 1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 50

Ala Ala Lys Glu Tyr Ala Ala Tyr Lys Ala Ala Ala Ala Ala Ala
 1               5                  10                  15

<210> SEQ ID NO 51
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 51

Glu Ala Ala Lys Tyr Ala Ala Tyr Lys Ala Ala Ala Ala Ala Ala
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 52

Glu Ala Lys Ala Tyr Ala Ala Tyr Lys Ala Ala Ala Ala Ala Ala
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 53

Glu Lys Ala Ala Tyr Ala Ala Tyr Lys Ala Ala Ala Ala Ala Ala
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 54

Glu Ala Glu Ala Tyr Ala Ala Tyr Lys Ala Ala Ala Ala Ala Ala
 1               5                  10                  15

<210> SEQ ID NO 55
```

```
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 55

Glu Ala Ala Glu Tyr Ala Ala Tyr Lys Ala Ala Ala Ala Ala Ala
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 56

Glu Glu Ala Ala Tyr Ala Ala Tyr Lys Ala Ala Ala Ala Ala Ala
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 57

Glu Glu Ala Lys Tyr Ala Ala Tyr Lys Ala Ala Ala Ala Ala Ala
 1               5                  10                  15

<210> SEQ ID NO 58
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 58

Glu Lys Glu Ala Tyr Ala Ala Tyr Lys Ala Ala Ala Ala Ala Ala
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 59

Ala Ala Lys Ala Tyr Glu Ala Tyr Lys Ala Ala Ala Ala Ala Ala
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 60

Ala Ala Glu Ala Tyr Lys Ala Tyr Lys Ala Ala Ala Ala Ala Ala
 1               5                  10                  15

<210> SEQ ID NO 61
<211> LENGTH: 15
```

```
<212> TYPE: PRT
<213> ORGANISM: Artificial Sequence
<220> FEATURE:
<223> OTHER INFORMATION: The peptide was designed and synthesized.

<400> SEQUENCE: 61

Glu Ala Lys Ala Tyr Glu Ala Tyr Lys Ala Ala Ala Ala Ala Ala
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 62

Glu Ala Glu Ala Tyr Lys Ala Tyr Lys Ala Ala Ala Ala Ala Ala
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 63

Glu Ala Ala Ala Tyr Lys Ala Tyr Lys Ala Ala Ala Ala Ala Ala
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 64

Glu Ala Ala Lys Tyr Glu Ala Tyr Lys Ala Ala Ala Ala Ala Ala
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 65

Glu Lys Ala Lys Tyr Glu Ala Tyr Lys Ala Ala Ala Ala Ala Ala
 1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 66

Glu Ala Lys Lys Tyr Glu Ala Tyr Lys Ala Ala Ala Ala Ala Ala
 1               5                  10                  15

<210> SEQ ID NO 67
<211> LENGTH: 15
<212> TYPE: PRT
```

<213> ORGANISM: Artificial Sequence
<220> FEATURE:
<223> OTHER INFORMATION: The peptide was designed and synthesized.

<400> SEQUENCE: 67

Ala Lys Lys Glu Tyr Ala Glu Tyr Lys Ala Ala Ala Ala Ala Ala
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 68

Ala Ala Glu Lys Tyr Ala Glu Tyr Lys Ala Ala Ala Ala Ala Ala
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 69

Glu Asn Pro Val Val His Tyr Phe Lys Asn Ile Val Thr Pro Arg
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 70

Glu Glu Lys Ala Tyr Ala Tyr Ala Lys Ala Ala Ala Ala Ala Ala
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 71

Glu Glu Ala Ala Tyr Lys Ala Ala Lys Ala Ala Ala Ala Ala Ala
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 72

Glu Glu Lys Ala Tyr Ala Ala Ala Lys Ala Ala Ala Ala Ala Ala
1               5                   10                  15

<210> SEQ ID NO 73
<211> LENGTH: 15
<212> TYPE: PRT
<213> ORGANISM: Artificial Sequence

```
<220> FEATURE:
<223> OTHER INFORMATION: The peptide was designed and synthesized.

<400> SEQUENCE: 73

Glu Glu Lys Ala Tyr Ala Ala Lys Ala Ala Ala Ala Ala Ala Ala
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 74

Glu Glu Ala Ala Tyr Lys Ala Ala Lys Ala Ala Ala Ala Ala Ala
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 75

Glu Glu Ala Ala Tyr Ala Tyr Lys Lys Ala Ala Ala Ala Ala Ala
 1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 76

Glu Ala Lys Ala Tyr Glu Tyr Ala Lys Ala Ala Ala Ala Ala Ala
 1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 77

Ala Ala Glu Lys Val Ala Ala Ala Ala Ala Ala Ala Ala Ala Ala
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 78

Ala Ala Ala Lys Tyr Ala Ala Ala Ala Ala Ala Ala Ala Ala Ala
 1               5                  10                  15

<210> SEQ ID NO 79
<211> LENGTH: 15
<212> TYPE: PRT
<213> ORGANISM: Artificial Sequence
<220> FEATURE:
```

-continued

<223> OTHER INFORMATION: The peptide was designed and synthesized.

<400> SEQUENCE: 79

Ala Ala Ala Lys Val Ala Ala Ala Ala Ala Ala Ala Ala Ala Ala
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 80

Ala Ala Glu Ala Tyr Ala Ala Ala Ala Ala Ala Ala Ala Ala Ala
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 81

Ala Ala Glu Ala Val Ala Ala Ala Ala Ala Ala Ala Ala Ala Ala
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 82

Ala Ala Glu Lys Ala Ala Ala Ala Ala Ala Ala Ala Ala Ala Ala
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 83

Glu Ala Pro Ala Tyr Lys Ala Tyr Lys Ala Ala Ala Ala Pro Ala
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 84

Glu Ala Pro Lys Tyr Glu Ala Tyr Lys Ala Ala Ala Ala Pro Ala
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: The peptide was designed and synthesized.

```
<400> SEQUENCE: 85

Glu Lys Pro Lys Tyr Glu Ala Tyr Lys Ala Ala Ala Ala Pro Ala
 1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 86

Glu Ala Pro Lys Tyr Glu Ala Tyr Lys Ala Ala Ala Ala Pro Ala
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 87

Ala Lys Pro Glu Tyr Ala Glu Tyr Lys Ala Ala Ala Ala Pro Ala
 1               5                  10                  15

<210> SEQ ID NO 88
<211> LENGTH: 17
<212> TYPE: PRT
<213> ORGANISM: Artificial Sequence
<220> FEATURE:
<223> OTHER INFORMATION: The peptide was designed and synthesized.

<400> SEQUENCE: 88

Ala Pro Glu Lys Ala Lys Tyr Glu Ala Tyr Lys Ala Ala Ala Ala
 1               5                  10                  15

Ala

<210> SEQ ID NO 89
<211> LENGTH: 19
<212> TYPE: PRT
<213> ORGANISM: Artificial Sequence
<220> FEATURE:
<223> OTHER INFORMATION: The peptide was designed and synthesized.

<400> SEQUENCE: 89

Ala Pro Glu Lys Ala Lys Tyr Glu Ala Tyr Lys Ala Ala Ala Ala
 1               5                  10                  15

Ala Pro Ala

<210> SEQ ID NO 90
<211> LENGTH: 17
<212> TYPE: PRT
<213> ORGANISM: Artificial Sequence
<220> FEATURE:
<223> OTHER INFORMATION: The peptide was designed and synthesized.

<400> SEQUENCE: 90

Glu Lys Ala Lys Tyr Glu Ala Tyr Lys Ala Ala Ala Ala Ala Pro
 1               5                  10                  15

Ala

<210> SEQ ID NO 91
```

```
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 91

Glu Lys Pro Lys Phe Glu Ala Tyr Lys Ala Ala Ala Ala Pro Ala
 1               5                  10                  15

<210> SEQ ID NO 92
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 92

Glu Lys Ala Lys Glu Glu Ala Tyr Lys Ala Ala Ala Ala Ala Ala
 1               5                  10                  15

<210> SEQ ID NO 93
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 93

Glu Lys Pro Lys Val Glu Ala Tyr Lys Ala Ala Ala Ala Pro Ala
 1               5                  10                  15

<210> SEQ ID NO 94
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 94

Glu Lys Pro Lys Glu Glu Ala Phe Lys Ala Ala Ala Ala Pro Ala
 1               5                  10                  15

<210> SEQ ID NO 95
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 95

Glu Lys Ala Lys Phe Glu Ala Phe Lys Ala Ala Ala Ala Ala Ala
 1               5                  10                  15

<210> SEQ ID NO 96
<211> LENGTH: 17
<212> TYPE: PRT
<213> ORGANISM: Artificial Sequence
<220> FEATURE:
<223> OTHER INFORMATION: The peptide was designed and synthesized.

<400> SEQUENCE: 96

Ala Pro Glu Lys Ala Lys Phe Glu Ala Phe Lys Ala Ala Ala Ala Pro
 1               5                  10                  15

Ala
```

```
<210> SEQ ID NO 97
<211> LENGTH: 17
<212> TYPE: PRT
<213> ORGANISM: Artificial Sequence
<220> FEATURE:
<223> OTHER INFORMATION: The peptide was designed and synthesized.

<400> SEQUENCE: 97

Ala Pro Glu Lys Ala Lys Phe Glu Ala Tyr Lys Ala Ala Ala Ala Pro
 1               5                  10                  15
Ala

<210> SEQ ID NO 98
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 98

Glu Ala Pro Lys Phe Glu Ala Tyr Lys Ala Ala Ala Ala Pro Ala
 1               5                  10                  15

<210> SEQ ID NO 99
<211> LENGTH: 15
<212> TYPE: PRT
<213> ORGANISM: Artificial Sequence
<220> FEATURE:
<223> OTHER INFORMATION: The peptide was designed and synthesized.

<400> SEQUENCE: 99

Glu Ala Pro Lys Val Glu Ala Tyr Lys Ala Ala Ala Ala Pro Ala
 1               5                  10                  15
```

US 7,456,252 B2

THERAPEUTIC PEPTIDES FOR DEMYELINATING CONDITIONS

RELATED APPLICATION

This application is a continuation of and claims the benefit of U.S. application Ser. No. 10/056,583, filed in the U.S. Patent and Trademark Office on Jan. 24, 2002, now U.S. Pat. No. 6,930,168 issued Aug. 16, 2005, which claims the benefit of provisional patent application No. 60/263,569 filed in the U.S. Patent and Trademark Office on Jan. 24, 2001, the entire contents of each of which are hereby incorporated herein by reference.

GOVERNMENT FUNDING

This invention was made in part with government support under grant CA-47554 awarded by the National Institutes of Health. The government has certain rights in the invention.

TECHNICAL FIELD

The invention relates to synthetic peptides for treatment of demyelinating autoimmune disease such as multiple sclerosis (MS).

BACKGROUND

MS is a chronic inflammatory disease of the central nervous system characterized by prominent lymphocyte and macrophage infiltration into the white matter and by demyelination. This pathology is associated with neurological dysfunctions such as paralysis, sensory deficit and visual problems. The cause of the disease is unknown, but both environmental and genetic factors are important. Previous studies demonstrated that the HLA-DR2 (DRB1*1501) haplotype, an allele of a multi-gene family encoding antigen receptors known as MHC class II proteins, is present at increased frequency in northern European patients with MS (Spielman R. S., Nathenson N., Epidemiol. Rev. 4:45 (1982); Hillert J. et al., J. Neuroimmunol. 50:95 (1994); Oksenberg J. R. et al., JAMA 270:2362 (1993)).

Peptides that bind to MHC class II proteins have specific types of amino acid side chains at locations in the peptide sequence that are known as anchor positions. A variety of side chains at non-anchor positions are permitted, some of which are presented to T cells in a further step of an immune response (Rudensky A. Y. et al., Nature (London) 353:622 (1991); Hammer J. et al., J. Exp. Med. 176:1007 (1992); Hammer J. et al., Cell 74:197 (1993); Chicz R. M. et al., Nature (London) 358:764 (1992); Chicz R. M. et al., J. Exp. Med. 178: 27 (1993); Malcherec G. et al., Int. Immunol. 5:1229 (1993); Falk K. et al., Immunogenetics 39:230 (1994)). Approximately 350,000 people in the U.S. and 2.5 million people worldwide suffer from MS, which typically affects females who reside in Northern latitudes, from about age 20. Strategies for inducing immunological tolerance include blocking antigen presentation, supplying altered peptide ligands, developing tolerance by i.v. and oral administration, and blocking costimulatory molecules (Sakai K. et al., Proc. Natl. Acad. Sci. U.S.A. 86:9470 (1989); Hurtenbach U. et al., J. Exp. Med. 177:1499 (1993); Fairchild P. J. et al., Immunology 81:487 (1994); Brocke S. et al., Nature 379:343 (1996)).

However, there is no cure for MS, a disease which is ultimately fatal. There is a need for improved agents to treat MS and other demyelinating conditions.

BRIEF DESCRIPTION OF THE DRAWINGS

FIG. 3A on the right is a line graph that shows inhibition of biotinylated MBP 85-99 binding to HLA-DR2 molecules as a function of concentration of synthetic peptide #101 (designated #1 in the FIG., solid triangles; SEQ ID NO: 65); #4 (SEQ ID NO: 92); #6 (SEQ ID NO: 94); and #7 (SEQ ID NO: 95).

FIG. 5A is a bar graph showing data obtained for inhibition of binding of biotinylated MBP 85-99 to HLA-DR2 molecules peptides at a concentration of 1.3 .mu.M for each of unlabeled peptides MBP 85-99 (SEQ ID NO: 1); #3 (SEQ ID NO: 91); #5 (SEQ ID NO: 93); #13 (SEQ ID NO: 98); and #14 (SEQ ID NO: 99). FIG. 5B is a line graph that shows the inhibition of proliferation of HLA-DR2 restricted MBP 84-102-specific T cell transfectant 8073 as a function of the concentration of each of synthetic peptides: #3 (SEQ ID NO: 91); #5 (SEQ ID NO: 93); #13 (SEQ ID NO: 98); and #14 (SEQ ID NO: 99). The data show that for peptides that are otherwise identical in sequence, substitution of an A residue at the P-3 position (peptide #13) for a K residue (#3) confers a greater inhibitory activity, if the P1 position residue is F; if the P1 position residue is V, substitution of A at P-3 provides at least as great inhibitory activity compared to a reference peptide having a K residue at P-3.

SUMMARY

Figure 1:
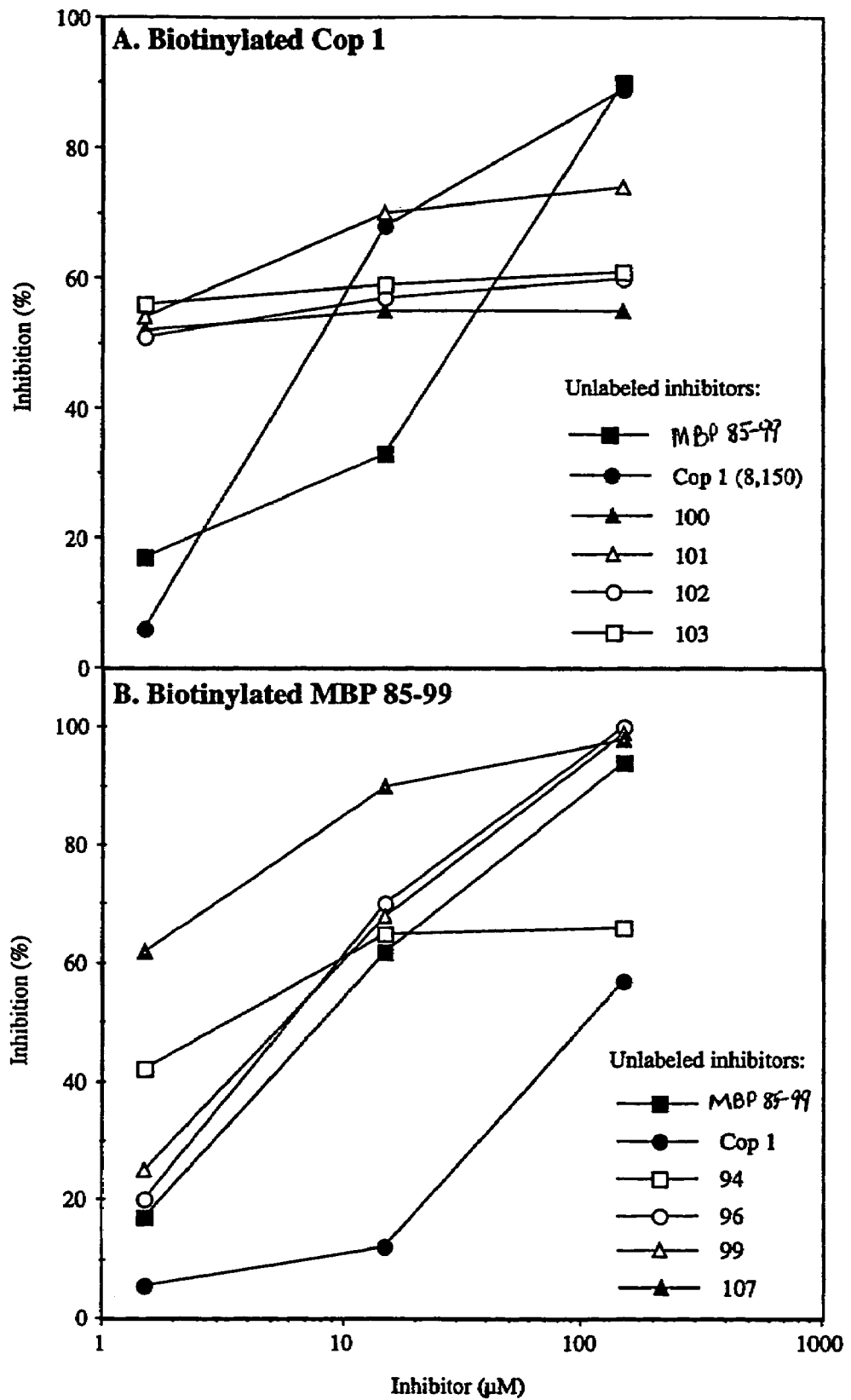
FIG. 1 is a line graph that shows the inhibition of biotinylated Cop 1 (FIG. 1A) and MBP 85-99 (FIG. 1B; SEQ ID NO: 1) binding to HLA-DR2 molecules as a function of concentration of unlabeled Cop 1 or each of the synthetic peptides: MBP 85-99 (SEQ ID NO: 1); and #100-#103 (SEQ ID NOs: 64-67, respectively).

The invention in one embodiment features a composition comprising a peptide with an amino acid sequence having two tyrosine (Y) residues and a lysine (K) residue, such that in a complex of the peptide with an MHC class II HLA-DR2 protein involved in modulation of an immune response, the residues in the amino acid sequence corresponding to: (i) tyrosines located at P1 and P4 positions; and (ii) lysine located at a P5 position which contacts a T cell receptor protein. A related embodiment features a peptide with an amino acid sequence having at least a tyrosine (Y) residue, a valine residue (V), and a lysine (K) residue, such that in a complex of the peptide with an MHC class II HLA-DR2 protein involved in modulation of an immune response, the residues in the amino acid sequence corresponding to: (i) valine located at a P1 position; (ii) tyrosine located at a P4 position; and (iii) lysine located at a P5 position which contacts a T cell receptor.

The "P1" position in the peptide is named by analogy to the amino acid location in an immunodominant epitope for an MHC class II HLA-DR2 protein associated with MS, the MBP 85-99 peptide (SEQ ID NO: 1), in which a valine (V) at position 89 fits into the "P1" pocket in the groove or cleft of the protein in a complex formed between this peptide and protein, and this V is therefore identified as being located at a P1 position. Other positions in the peptide are named based on the location relative to the P1 position, i.e., a phenylalanine (F) at position 92 (further toward the carboxy terminus, or downstream from P1) of MBP is in the P4 position, and the amino acid adjacent to P1 but further toward the amino terminus, or upstream, is referred to as being in the P–1 (P minus one) position.

In examples of the above embodiments, the sequence further comprises a lysine (K) residue at a P–1 position; the sequence of the peptide further includes a plurality of alanine (A) residues at positions which are to the carboxy-terminal side of the lysine residue at P5. In further embodiments, the peptide is substantially pure; the peptide is synthetic. The composition comprises an additional therapeutic agent, for example, the additional therapeutic agent is selected from the group consisting of an interferon and a random heteropolymer of amino acids.

The invention in another embodiment provides a composition comprising a synthetic peptide, wherein the peptide has an amino acid sequence having a greater inhibitory activity for binding to the antigen binding groove of an MHC class II HLA-DR2 protein associated with multiple sclerosis, than a reference material selected from the group of: an immunodominant epitope from myelin basic protein (MBP), the epitope comprising MBP residues 85-99 ENPVVH-FFKNIVTPR as shown in SEQ ID NO: 1; and a randomly polymerized amino acid heteropolymer having amino acids, tyrosine, alanine, glutamic acid, and lysine (Copaxone®), the composition further capable of inhibiting proliferation of an MBP-specific T cell.

For example, the greater inhibitory activity of the peptide than the reference material is at least 10%; or is at least 20%. Further, the peptide is about 5 to about 100 amino acids in length; for example, the peptide is about 5 to about 25 amino acids in length; for example, the peptide is about 5 to about 15 amino acids in length. In certain embodiments, the peptide further comprises at least one non-naturally occurring amino acid, in a location in the sequence and in an amount sufficient to inhibit proteolytic degradation of the peptide in a subject, in comparison with a peptide identical in sequence and consisting of naturally occurring amino acid residues. Alternatively, the peptide comprises at least one non-naturally occurring amino acid, in a location in the sequence and in an amount sufficient to increase the affinity for the antigen binding groove of the MHC class II HLA-DR2 protein, in comparison with a peptide identical in sequence and consisting of naturally occurring amino acid residues. The at least one non-naturally occurring amino acid is the presence of at least one D-amino acid within four residues of at least one of the carboxy-terminal and amino-terminal.

In further embodiments, the composition comprises a plurality of copies of the peptide as a monomer unit of an oligomer, each monomer unit being joined by a flexible linker. For example, the oligomer is a homo-oligomer. Alternatively, the oligomer is a hetero-oligomer. The peptide can further comprise the presence in the sequence of at least one proline residue. Further, the at least one proline residue is present proximal to at least one of carboxy- and amino-termini of the sequence, i.e., the at least one proline is at a position within at most four residues of at least one of carboxy and amino termini.

The peptide can further comprise at least one non-peptide bond. The non-peptide bond is selected from the group consisting of a peptide nucleic acid bond and a phosphorothioate bond.

The non-naturally occurring amino acid can be a substitution of at least one alanine (A) in the sequence with a peptidomimetic compound selected from the group consisting of: Tic, which is tetrahydroisoquinoline-(S)-3-carboxylic acid); Thiq, which is tetrahydroisoquinoline-(S)-1-carboxylic acid); Disc, which is (dihydroisoindole-(S)-2-carboxylic acid); C(Acm), which is acetamido-methyl-Cys; C(Pmm), which is propylamidomethyl-Cys; C(Ace), which is acetyl-Cys; MePhg, which is methylphenyl-Gly; and Nva, which is norvaline. The amino acid modification is N-methylation of a peptide backbone nitrogen.

The invention in another embodiment features a composition comprising a synthetic peptide having an amino acid sequence selected from the group consisting of:

| | |
|---|---|
| AAEAYKAYKAAAAAA, | (SEQ ID NO: 60) |
| EAAAYKAYKAAAAAA, | (SEQ ID NO: 63) |
| EAAKYEAYKAAAAAA, | (SEQ ID NO: 64) |
| EKAKYEAYKAAAAAA, | (SEQ ID NO: 65) |
| EAKKYEAYKAAAAAA, | (SEQ ID NO: 66) |
| AKKEYAEYKAAAAAA, | (SEQ ID NO: 67) |
| EAPAYKAYKAAAAPA, | (SEQ ID NO: 83) |

-continued

```
EAPKYEAYKAAAAPA,       (SEQ ID NO: 84)

EKPKYEAYKAAAAPA,       (SEQ ID NO: 85)

EAPKYEAYKAAAAPA,       (SEQ ID NO: 86)

AKPEYAEYKAAAAPA,       (SEQ ID NO: 87)

APEKAKYEAYKAAAAAA,     (SEQ ID NO: 88)

APEKAKYEAYKAAAAAPA,    (SEQ ID NO: 89)

EKAKYEAYKAAAAAPA,      (SEQ ID NO: 90)

EKPKFEAYKAAAAPA,       (SEQ ID NO: 91)

EKAKYEAYKAAAAAA,       (SEQ ID NO: 92)

EKPKVEAYKAAAAPA,       (SEQ ID NO: 93)

EKPKEEAFKAAAAPA,       (SEQ ID NO: 94)

EKAKFEAFKAAAAAA,       (SEQ ID NO: 95)

APEKAKFEAFKAAAAPA,     (SEQ ID NO: 96)

APEKAKFEAYKAAAAPA,     (SEQ ID NO: 97)

EAPKFEAYKAAAAPA,       (SEQ ID NO: 98)
and

EAPKVEAYKAAAAPA.       (SEQ ID NO: 99)
```

Further, the peptide is substantially pure. The above selected peptide can further comprise substitution of a tyrosine (Y) in the P1 position by a valine (V). In a related embodiment, the above peptide comprises an oligomer having a plurality of monomer units having the amino acid sequence of the synthetic peptide, the units joined by a flexible linker. The invention also features a method for reducing demyelination of cells in a subject, the method comprising administering to the subject a composition as shown above.

Another embodiment of the invention features a method for obtaining a synthetic peptide having inhibitory activity for binding of an immunodominant epitope of multiple sclerosis (MS) to an MHC class II protein associated with MS, the method comprising:

designing a plurality of peptide sequences, wherein each peptide comprises a sequence of amino acids having a charge, size, and order within the sequence such that the peptide is capable of occupying features of an antigen binding site of an MHC class II protein associated with multiple sclerosis (MS); and assaying each of the plurality of peptides for affinity for the MHC class II protein, to determine the amount of the peptide having inhibitory activity for binding of a reference compound to the MHC class II protein, wherein a lower amount of peptide able to inhibit the extent of binding compared to the reference compound indicates a greater inhibitory activity of the peptide for inhibiting binding of an immunodominant epitope of multiple sclerosis (MS) to an MHC class II protein associated with MS.

Yet another embodiment is a method for obtaining a synthetic peptide having inhibitory activity for proliferation of cells of a T cell line, the T cells restricted to an immunodominant epitope of multiple sclerosis (MS), the method comprising:

designing a plurality of peptide sequences, wherein each peptide comprises a sequence of amino acids having a charge, size, and order within the sequence such that the peptide is capable of occupying features of an antigen binding site of an MHC class II protein associated with multiple sclerosis (MS); and assaying each of the plurality of peptides for an amount that has ability to inhibit proliferation of the T cells, wherein a lower amount of peptide able to inhibit the proliferation of the cells compared to the reference compound indicates a greater inhibitory activity of the peptide for inhibiting the T cells restricted to an immunodominant epitope of multiple sclerosis (MS).

In related embodiments of these methods, the reference compound is selected from a group consisting of Copaxone® and a peptide comprising a sequence of amino acids at positions 85-99 of myelin basic protein (MBP) as shown in SEQ ID NO: 1. The methods can further comprise: measuring an ability of each of the plurality of peptides to inhibit presentation of the reference compound to HLA restricted T cells. The methods can further comprise designing a plurality of peptide sequences having a charge, a size, and an order within the sequence, by choosing amino acids to occupy positions in the sequence of that peptide capable of contacting the antigen binding P1 and P4 pockets of the MHC class II protein associated with MS, corresponding to locations in the MBP 85-99 peptide amino acid sequence at residues 89 and 92, respectively. For example, the methods comprise selecting the amino acids contacting the P1 and P4 pockets from the group consisting of hydrophobic amino acids; for example, the hydrophobic amino acids are selected from the group consisting of a tyrosine (Y), a valine (V), a phenylalanine (F), a methionine (M), an isoleucine (I), and a leucine (L). The hydrophobic amino acids contacting the P4 pocket are selected from the group consisting of a tyrosine (Y) and a phenylalanine (F). In one example, the amino acid contacting the P1 pocket is valine (V). Further, the amino acid in the P5 position is a lysine (K). In comparing the affinity of each of the plurality of peptides, the method further comprises providing a reference compound having a detectable modification. For example, the modification is selected from the group of compounds which are radioactive, antigenic, biotinylated, fluorescent, photometric, and have a high affinity for an immobilized ligand.

A further embodiment of the method is determining the concentration of the peptide able to inhibit an extent of binding of the test compound to the MHC class II protein associated with multiple sclerosis, the method further comprises measuring an amount of proliferation of a DR2-restricted cell line of T cells exposed to the complex of the peptide with the MHC class II protein. Thus measuring the amount of proliferation further comprises determining an amount of IL-2 secretion by the T cells. Further, determining the amount of IL-2 secretion further comprises assaying culture fluid of the T cells for ability to support growth of IL-2 dependent cytotoxic T-cell interleukin-dependent lymphocytes (CTLL). In this assay, the lower the amount of IL-2 secretion, the greater the extent the peptide is able to inhibit proliferation of the T cells.

Another feature of the invention provides a method of treating a subject having a demyelinating condition, comprising: providing to the subject a composition capable of inhibiting binding of myelin basis protein (MBP) peptide to purified recombinant MHC class II DR2 molecules, wherein the composition is a peptide that comprises an amino acid sequence selected from the group consisting of: AAE-AYKAYKAAAAAA (SEQ ID NO: 60), EAAAYKAY-KAAAAAA (SEQ ID NO: 63), EAAKYEAYKAAAAAA (SEQ ID NO: 64), EKAKYEAYKAAAAAA (SEQ ID NO: 65), EAKKYEAYKAAAAAA (SEQ ID NO: 66), AKKEYAEYKAAAAAA (SEQ ID NO: 67), EAPAYKAY-KAAAAPA (SEQ ID NO: 83), EAPKYEAYKAAAAPA (SEQ ID NO: 84), EAPKYEAYKAAAAPA (SEQ ID NO: 86), AKPEYAEYKAAAAPA (SEQ ID NO: 87), APEKAK-YEAYKAAAAAA (SEQ ID NO: 88), APEKAKYEAY-KAAAAAAPA (SEQ ID NO: 89), EKAKYEAY-KAAAAAAPA (SEQ ID NO: 90), EKPKFEAYKAAAAPA (SEQ ID NO: 91), EKPKVEAYKAAAAPA (SEQ ID NO: 93), EKAKFEAFKAAAAAA (SEQ ID NO: 95), APEKAK-FEAFKAAAAPA (SEQ ID NO: 96), and APEKAKFEAY-KAAAAPA (SEQ ID NO: 97), wherein the subject having a demyelinating condition is treated. The demyelinating condition is selected from the group consisting of a post-viral encephalomyelitis, a post-vaccine demyelinating condition, a multiple sclerosis, and a side effect of administering an anti-TNF agent. The MBP peptide comprises MBP residues 85-99 as shown in SEQ ID NO: 1. In a related embodiment, the peptide further inhibits proliferation of autoantigen-specific HLA-DR2-restricted T cell clones. In yet another related embodiment, the amino acid sequence of the peptide selected above further comprises at least one amino acid analog substituted for an amino acid. Alternatively, the amino acid sequence of the peptide comprises at least one peptide bond analog.

The method further comprises formulating the composition in a pharmaceutically acceptable carrier. The method further comprises formulating the composition as a unit dose. In these methods, the MHC class II DR2 molecules are of a genotype associated with multiple sclerosis. For example, the MHC class II DR2 molecules are selected from the group consisting of DRB1*1501 and DRB1*1602.

Another featured embodiment of the invention herein is a kit comprising at least one container having a peptide capable of inhibiting binding of an immunodominant epitope of myelin basic protein to an MHC class II DR2 protein, and instructions for use. The peptide can be substantially pure. Further, the kit comprises a peptide in a pharmaceutically acceptable buffer, and instructions for use.

DETAILED DESCRIPTION OF SPECIFIC EMBODIMENTS

Definitions

Unless the context otherwise requires, as used in this description and in the following claims, the terms below shall have the meanings as set forth:

The term "autoimmune condition" means a disease state caused by an inappropriate immune response that is directed to a self-encoded entity which is known as an autoantigen.

The term "demyelinating condition" includes a disease state in which a portion of the myelin sheath, consisting of plasma membrane wrapped around the elongated portion of the nerve cell, is removed by degradation. A demyelinating condition can arise post-vaccination, post-anti TNF treatment, post-viral infection, and in MS.

Symptoms of MS include weakness, spasticity, fatigue, numbness, pain, ataxia, tremor, depression, speech, vision and cognitive disturbances, dizziness, and bladder, bowel and sexual dysfunction. MS can be episodic, each episode followed by a period of remission, with symptoms worsening in each episode (remitting-relapsing), culminating in death.

The term "anergy" means unresponsiveness of the immune system of a subject to an antigen.

The term "subject" means a mammal, preferably a human. The term "patient" refers to a human having an autoimmune disease such as a demyelinating condition, such as MS.

The phrases "amino acid" and "amino acid sequence" can include one or more components which are amino acid derivatives and/or amino acid analogs comprising part or the entirety of the residues for any one or more of the 20 naturally occurring amino acids indicated by that sequence. For example in an amino acid sequence having one or more tyrosine residues, a portion of one or more of those residues can be substituted with homotyrosine. Further, an amino acid sequence having one or more non-peptide or peptidomimetic bonds between two adjacent residues, is included within this definition.

The term "hydrophobic" amino acid means aliphatic amino acids alanine (A or ala), glycine (G or gly), isoleucine (I or ile), leucine (L or leu), methionine (M or Met), proline (P or pro), and valine (V or val), the terms in parentheses being the one letter and three letter standard code abbreviations for each amino acid, and aromatic amino acids tryptophan (W or trp), phenylalanine (F or phe), and tyrosine (Y or tyr). These amino acids confer hydrophobicity as a function of the length of aliphatic and size of aromatic side chains, when found as residues within a protein.

The term "charged" amino acid means amino acids aspartic acid (D or asp), glutamic acid (E or glu), histidine (H or his), arginine (R or arg) and lysine (K or lys), which confer a positive (his, lys, and arg) or negative (asp, gly) charge at physiological values of pH in aqueous solutions on proteins containing these residues.

The term "derivative" of an amino acid means a non-naturally occurring chemically related form of that amino acid having an additional substituent, for example, an N-carboxyanhydride group, a γ-benzyl group, an ε,N-trifluoroacetyl group, or a halide group attached to an atom of the amino acid.

The term "analog" means a non-naturally occurring non-identical but chemically related form of the reference amino acid. For example, the analog can have a different steric configuration, such as an isomer of an amino acid having a D-configuration rather than an L-configuration, or an organic molecule with the approximate size and shape of the amino acid, or an amino acid with modification to the atoms that are involved in the peptide bond, so as to be protease resistant when polymerized in the context of a peptide or polypeptide.

Purified MHC class II HLA-DR2 protein is used as a basis herein to design and to identify peptide compositions having potential therapeutic activity, as determined by binding in competition with a test compound that is a peptide having the amino acid sequence of myelin basic protein (MBP) residues 85-99, or with a test compound that is Cop 1 (Copaxone®).

The term "heterologous cell" refers to an unrelated recombinant cell for expression of a gene encoding one or more subunits of an MHC protein of a mammal, for example, a human. The heterologous cell is preferably not mammalian, more preferably the heterologous cell is not from a warm blooded animal, even more preferably the heterologous cell is not from a vertebrate animal. In a preferred embodiment the heterologous cell is an insect cell such as an Sf8 cell, or a cell of a microorganism such as a yeast cell (e.g., a cell of a species of *Saccharomyces* or a species of *Pichia*). Following expression and production of MHC protein in a heterologous cell, the protein is free of any epitopes found in a mammal such as a human. Because the MHC protein is in an uncomplexed "empty" form, it is available for binding to the synthetic peptides of the present invention.

The term "surfaces of MHC class II HLA-DR2 protein" includes the portions of the protein molecule in its 3-dimensional configuration which are in contact with its external environment. For example, the surfaces include amino acid residues found in features of the protein that interact with aqueous solvent and are capable of binding to other cell components such as nucleic acids, other proteins, and peptides.

The terms "P1 pocket" and "P4 pocket" refer to regions of the epitope binding cleft formed at the intersection of the α and β sunits, in the three dimensional polymorphic region of the peptide binding surface of the MHC class II protein molecule that accommodates amino acid residue side chains from a peptide that is bound to the MHC class II protein (Fridkis-Hareli, M. et. al., Human Immunol. 61:640 (2000)). The peptide that bind include a naturally occurring antigen or epitope, and a bound synthetic peptide. A reference peptide for the MHC class II DR-2 molecules herein is MBP 85-99 having the sequence ENPVVHFFKNIVTPR (SEQ ID NO: 1; Table 1; FIG. 3B). In a complex of the 15-mer peptide MBP 85-99 with MHC class II protein, the V at position 89 of MBP 85-99 is located in the P1 pocket of MHC class II Dr-2 protein. In a complex of the MHC class II protein with another peptide, an amino acid residue in the sequence of the peptide having this property is referred to herein as being located in the "P1 position" of that peptide. In a complex of the 15-mer peptide MBP 85-99 with MHC class II protein, the F at position 93 MBP 85-99 is similarly located in the P4 pocket. In a complex of the MHC class II protein with another peptide, an amino acid residue in the sequence of the peptide having this property is referred to herein as being located in the "P4" position of that peptide.

The terms "P–1 position" (i.e., the "P minus 1" position, referring to the amino acid residue adjacent to the amino acid residue at the P1 position) and "P5 position" refer functionally to amino acid residues in the peptide which is capable of binding to a MHC class II protein molecule to form a complex, and which directly contact the T-cell receptor (Fridkis-Hareli, M. et. al., Human Immunol. 61:640 (2000)). Structurally, the P–1 position refers to the amino acid which is adjacent to, and to the N-terminus side of, the amino acid P1 position, i.e., the P1 position being occupied by an amino acid residue in the peptide sequence that occupies the P1 pocket. Similarly, the P–2 position ("P minus 2"), P–3 positions, etc. refer respectively to amino acids located in the peptide sequence which are adjacent to, and to the N-terminus side of, the amino acid residues of the peptide that is the P–1 position, P–2 position, respectively. The P5 position refers to the amino acid residue that is adjacent to, and to the C-terminus side of, the amino acid residue in the P4 position.

The term "antigen binding groove" refers to a three dimensional antigen interactive site on the surface of the MHC class II protein molecule (Stern, L. J. et. al., Nature 368:215 (1994)) that is formed by surfaces of both the α and β subunits of the MHC protein molecule.

The term "oligomer" includes a series of a plurality of peptide units, covalently, linked for example, by peptide bonds. The term "homo-oligomer" includes an oligomer in which the sequence unit that is repeated is identical in all units. The term "hetero-oligomer" includes an oligomer in which the peptide units that are repeated are not identical in amino acid sequence. The term "flexible molecular linker" includes linkers that have backbone lengths of about 50-80 Å, extending to 540 Å, to 750 Å, or greater. If composed of amino acids residues, the linker may contain 10-20 residues, 20-50 residues, or 50-125 residues. The linkers can also be composed of components other than amino acids, for example, the linkers can comprise a polymer or a copolymer of organic acids, aldehydes, alcohols, thiols, and/or amines; polymers or copolymers of hydroxy-, amino-, and/or di-carboxylic acids; a polymer or a copolymer of saturated or unsaturated hydrocarbons; a polymer or a copolymer of naturally and non-naturally occurring amino acids. The linkers are described in PCT/US97/13885 (Feb. 12, 1998), which is hereby incorporated herein by reference.

The term "substantially pure" as refers to a composition herein means that the material of the composition is primarily composed of the composition, and is largely free of other chemical materials. In various aspects, the composition is at least 85% pure, at least 90% pure, at least 95% pure, at least 98% pure, or at least 99% pure. Purity can be assessed on the basis of weight, which can be determined by areas under a curve from a printout of an analytical instrument such as a gel reader, a chromatography column including gas chromatography, and other devices for purification known to those of skill in the biochemical arts.

While the peptides herein are referred to as "synthetic", for multiple reasons such as cost, the ease of preparation, ability to introduce non-naturally occurring amino acids and non-peptidic bonds, and high state of purity of materials produced by peptide synthesis, it is also possible to synthesize the materials herein by expression of a nucleic acid encoding the peptide, particularly for longer forms such as oligomers and polymers. Such recombinantly produced peptides, oligomers and polymers can be readily prepared by one of ordinary skill in the recombinant genetic arts, and are within the embodiments of the present invention.

Autoimmune Diseases

An autoimmune disease results when a host's immune response fails to distinguish foreign antigens from self molecules (autoantigens) thereby eliciting an aberrant immune response. The immune response towards self molecules results in a deviation from the normal state of self-tolerance, which arises when the production of T cells and B cells capable of reacting against autoantigens has been prevented by events that occur in the development of the immune system early in life. The cell surface proteins that play a central role in regulation of immune responses through their ability to bind and present processed peptides to T cells are the major histocompatibility complex (MHC) molecules (Rothbard, J. B. et al., Annu. Rev. Immunol. 9:527 (1991)).

A number of therapeutic agents have been developed to treat autoimmune diseases. For example, agents have been developed that can prevent formation of low molecular weight inflammatory compounds by inhibiting a cyclooxygenase. Also, agents are available that can function by inhibiting a protein mediator of inflammation by sequestering the inflammatory protein tumor necrosis factor (TNF) with an anti-TNF specific monoclonal, antibody fragment, or with a soluble form of the TNF receptor. Finally, agents are available that target and inhibit the function of a protein on the surface of a T cell (the CD4 receptor or the cell adhesion receptor ICAM-1) thereby preventing interaction with an antigen presenting cell (APC). However, compositions which are natural folded proteins as therapeutic agents can incur problems in production, formulation, storage, and delivery. Further, natural proteins can be contaminated with pathogenic agents such as viruses and prions.

An additional target for inhibition of an autoimmune response is the set of lymphocyte surface proteins represented by the MHC molecules. Specifically, these proteins are encoded by the MHC class II genes designated as HLA (human leukocyte antigen)-DR, -DQ and -DP. Each of the MHC genes is found in a large number of alternative or allelic forms within a mammalian population. The genomes of subjects affected with certain autoimmune diseases, for example, MS and rheumatoid arthritis (RA), are more likely to carry one or more characteristic MHC class II alleles, to which that disease is linked.

A potential source of agents for treatment of MS and other demyelinating conditions is to identify peptides that bind selectively in vitro to a purified MHC class II allele protein molecule, particularly to a protein which is a product of an MHC class II allele associated with demyelinating conditions. In addition, the agent should bind to that protein as it occurs on the surfaces of antigen presenting cells in vivo, and thereby block, anergize, or inactivate the class of T cells that are responsible for the demyelinating conditions, such as MS.

Major candidates for target antigens in MS include myelin basic protein (MBP), proteolipid protein (PLP), and myelin oligodendrocyte glycoprotein (MOG). T cells reactive with these antigens have been found both in normal blood (Wucherpfennig K. W. et al., J. Immunol. 150:5581 (1994); Steinman L. et al., Mol. Med. Today 1:79 (1995)) and in MS patients (Wucherpfennig K. W. et al., Immunol. Today 12:227 (1991); Marcovic-Plese S. et al., J. Immunol. 155:982 (1995); Correale J. et al., Neurology 45:1370 (1995); Kerlero de Rosbo N. et al., Eur. J. Immunol. 27:3059 (1997); Tsuchida T. et al., Proc. Natl. Acad. Sci. U.S.A. 91:10859 (1994)), suggesting that autoreactive T cells may be involved in the pathogenesis of the disease, such that these cells once activated can penetrate the blood-brain barrier. Microbial agents have been suggested to provide potential stimuli for induction of MS by immunological cross-reaction with MBP (Wucherpfennig K. W. et al., Cell 80:695 (1995); Brocke S. et al., Nature 365:642 (1993)).

Studies indicate that MBP is an important target antigen in the immunopathogenesis of MS. MBP-specific T cells have been shown to be clonally expanded in MS patients and in an in vivo activated state (Wucherpfennig K. W., et al., J. Immunol. 150:5581 (1994); Allegretta M. et al., Science 247:718 (1990); Ota K. et al., Nature 346:183 (1990); Zhang J. et al., J. Exp. Med. 179:973 (1994)). Reactivity with the immunodominant MBP 84-102 peptide is found predominantly in subjects carrying HLA-DR2, a genetic marker for susceptibility to MS. Structural characterization of MBP 84-102 identified residues critical for MHC class II binding and for TCR recognition (Wucherpfennig K. W. et al., J. Exp. Med. 179: 279 (1994)), which have been recently confirmed by the crystal structure of HLA-DR2 complexed with MBP 85-99 peptide (Smith K. J. et al., J. Exp. Med. 19:1511 (1998)).

An agent that interacts with and binds promiscuously to several MHC class II molecules is Copolymer 1 (Cop 1; YEAK; Copaxone®). This synthetic amino acid heteropolymer is capable of suppressing experimental allergic encephalomyelitis (EAE; Sela, M. et al., Bull. Inst. Pasteur (Paris) (1990)), a condition which can be induced in the mouse and is a model for MS. Cop 1, the random heteropolymer of amino acids known as poly(Y,E,A,K), indicated using the one letter amino acid code (Y is tyrosine, E is glutamic acid, A is alanine, and K is lysine) is a therapeutic agent for MS, but does not suppress the disease entirely (Bornstein, M. B. et al., N. Engl. J. Med. 317:408 (1987); Johnson, K. P. et al., Neurology 45:1268 (1995)).

Cop 1 binds to purified human HLA-DR molecules within the peptide binding groove and inhibits the binding of a high affinity epitope of influenza virus HA 306-318, to both HLA-DR1 (DRB1*0101) and -DR4 (DRB1*0401) molecules, and the binding of MBP 84-102, a human immunodominant epitope of MBP, to HLA-DR2 (DRB1*1501) molecules (Fridkis-Hareli M, et al., J Immunol 160:43864397, 1998). Copolymers composed of only three amino acids (for example, EAK, YEA, YAK and YEK) also bind to purified HLA-DR1, -DR2 and -DR4 molecules (Fridkis-Hareli M, et al. Int Immunol 11:635, 1999; PCT/US99/16,617). Moreover, these three amino acid copolymers compete with CII 261-273 for binding to RA-associated HLA-DR1 (DRB1*0101) and -DR4 (DRB1*0401) molecules, and also inhibited CII-reactive T cell clones (Fridkis-Hareli M, et al. Proc Natl Acad Sci USA 95:12528, 1998); PCT/US99/16617 and PCT/US99/16747.

The bound fraction of Cop 1, treated with aminopeptidase I, has been isolated from recombinant "empty" HLA-DR molecules produced in insect cells, and has been sequenced. The Cop 1 binding motif for HLA-DR2 showed increases in levels of E at the first and second cycles, of K at the second and third cycles, and of Y and A (presumably at P1 of the bound peptide) at the third to fifth cycle. No preference was seen at the following cycles which were mainly A (Fridkis-Hareli M, et al. J Immunol 162:4697, 1999; PCT/US99/16, 617). Recently, the characterization of the active component(s) of the mixture of random polypeptides was attempted by synthesis of a set of peptides based on Cop 1 binding properties to HLA-DR1 and -DR4 molecules (Fridkis-Hareli M, et al. Human Immunol 61: 640, 2000); PCT/US99/16,617. Several peptides inhibited binding of CII 261-273 epitope to DRB 1*0101 and -DR4 DRB1*0401 molecules and inhibited presentation of this epitope to CII-reactive DR1- and DR4-restricted T cell clones (Fridkis-Hareli M, et al. Human Immunol 61: 640, 2000).

Demyelinating conditions have been found to occur post-viral infection, post-vaccination, post-encephalomyelitis (Wucherpfenning K.W. et al., Immunol. Today 12:277-282 (1991)) and following administration of certain anti-TNF agents (FDA Talk Paper, Food and Drug Administration Public Health Service, Rockville, Md.).

Many derivatives of synthetic peptides having increased pharmacological life in vivo have been synthesized. The loading of MHC class II binding sites occurs in endosomal compartments abundant with proteases, particularly cathepsins. Peptides may be digested also by amino- or carboxy-peptidases in serum or other biological fluids. Therefore, proteolysis of the peptides may effectively remove the peptides from the subject (Bennett, K., et al., 1992, Eur. J. Immunol. 22:1519). To reduce or eliminate potential proteolysis, modification of the peptides, for example, N-methylation of backbone nitrogens in the peptides, which are not involved in essential hydrogen bonding interactions, could produce a peptide derivative that is resistant to proteolysis (Falconi, F., et al., 1999, Nature Biotechnology 17:562). In Falconi et al., N-methylation of a hemagglutinin (HA) peptide to produce a modified peptide derivative yielded a compound that was substantially less sensitive to digestion by cathepsin B. The resulting protease resistant peptide was also a substantially better inhibitor of presentation by MHC class II DR proteins to T-cell clones, compared to the original HA peptide.

In another embodiment, the invention provides derivatives of synthetic peptides having a chemical alteration in one or both of the peptide backbone or the amino acid side chains. These derivatives can have increased binding affinity to the MHC class II DR1 protein, result in increased inhibitory activity and/or resistance to proteolysis. This phenomenon was observed when a peptidomimetic compound was designed to replace a native hemagglutinin (HA) peptide in binding to an MHC class II DR1 protein (Falconi, F., et al., 1999, Nature Biotechnology 17:562). The designed peptide was comprised of suitable amino acid mimetic compounds for each of several particular amino acids. In one example, alanine (A) was substituted with one or more conformationally restricted aromatic compounds, Tic, which is tetrahydroisoquinoline-(S)-3-carboxylic acid), Thiq, which is tetrahydroisoquinoline-(S)-1-carboxylic acid), and Disc, which is (dihydroisoindole-(S)-2-carboxylic acid), and the blocked Cys compounds C(Acm), which is acetamido-methyl-Cys, C(Prm), which is propylamidomethyl-Cys, and C(Ace), which is acetyl-Cys. Furthermore, MePhg, which is methylphenyl-Gly, and Nva, which is norvaline, provided increased binding affinity. Substitution by some of the peptidomimetics resulted in improved inhibition of the immune response.

In various embodiments of the present invention, a series of peptides are designed having a sequence comprising amino acids tyrosine (Y), glutamic acid (E), alanine (A), and lysine (K), and further having replacements of Y with other hydrophobic residues, K with uncharged residues, and alanine (A) with prolines near the termini of the peptides. These additional peptides are tested for MHC class II HLA-DR2 binding by extent of inhibition of a labeled reference molecule having known affinity for HLA-DR2, and inhibition activity of presentation to T cells. Peptides are thereby obtained that show as least as great or increased binding affinity as the unmodified synthetic peptide, as well as an increased potency in inhibiting T-cell responses to processed protein antigens presented by the targeted MHC molecule.

Methods and Uses

The therapeutic compounds of the invention can be used to treat symptoms of multiple sclerosis, an MS demyelinating condition marked by patches or hardened tissue in the brain or the spinal cord; and other demyelinating conditions. Therapeutic compounds of the invention, while characterized by binding to MHC class II HLA-DR2 molecules, may have increased affinity for MHC class II molecules associated with additional autoimmune diseases.

A pharmaceutically acceptable carrier includes any and all solvents, dispersion media, coatings, antimicrobials such as antibacterial and antifungal agents, isotonic and absorption delaying agents and the like that are physiologically compatible. Preferably, the carrier is suitable for intravenous, intramuscular, oral, intraperitoneal, transdermal, or subcutaneous administration. The active compound can be coated in a material to protect it from inactivation by the action of acids or other adverse natural conditions.

A composition of the present invention can be administered by a variety of methods known in the art as will be appreciated by the skilled artisan. Copaxone®, for example, is supplied as an acetate form, and is reconstituted in aqueous solution and administered to an MS patient subcutaneously. The peptides herein can be similarly formulated and delivered. The peptide and any additional active compound as described herein to be administered in combination with the peptides can further be prepared with carriers that will protect it against rapid release, such as a controlled release formulation, including implants, transdermal patches, micro-encapsulated delivery systems. Many methods for the preparation of such formulations are patented and are generally known to those skilled in the art. See, e.g., *Sustained and Controlled Release Drug Delivery Systems*, J. R. Robinson, Ed. Marcel Dekker, Inc., NY (1978).

Therapeutic compositions for delivery in a pharmaceutically acceptable carrier are sterile, and are preferably stable under the conditions of manufacture and storage. The composition can be formulated as a solution, microemulsion, liposome, or other ordered structure suitable to high drug concentration. Dosage regimens can be adjusted to provide the optimum desired response (e.g., a therapeutic response). For example, a single bolus can be administered, several divided doses can be administered over time, or the dose can be proportionally reduced or increased as indicated by the exigencies of the disease situation.

In general, a preferred embodiment of the invention is to administer a suitable daily dose of a therapeutic synthetic peptide composition that will be the lowest effective dose to produce a therapeutic effect, for example, mitigation of symptoms. The therapeutic peptide compounds of the invention are preferably administered at a dose per subject per day of at least 2 mg, at least 5 mg, at least 10 mg or at least 20 mg as appropriate minimal starting dosages. In general, the compound of the effective dose of the composition of the invention can be administered in the range of 50 to 400 micrograms of the compound per kilogram of the subject per day.

A physician or veterinarian having ordinary skill in the art can readily determine and prescribe the effective dose of the pharmaceutical composition required. For example, the physician or veterinarian could start doses of the compound of the invention employed in the pharmaceutical composition at a level lower than that required in order to achieve the desired therapeutic effect, and increase the dosage with time until the desired effect is achieved.

A desired therapeutic effect can be determined by increased periods of remission of MS, such that fewer episodes of relapse per unit time are noted. Another desired therapeutic effect can be remission in symptoms such as pain, dizziness, fatigue, visual and cognitive disturbances as noted herein. Remissions of symptoms can be self-reported by the patient, or can be quantitatively detected by standard measurements of sensory and cognitive abilities, known to practitioners in the art of treating autoimmune conditions such as demyelinating conditions.

In another preferred embodiment, the pharmaceutical composition includes also an additional therapeutic agent. Thus in a method of the invention, the pharmaceutical composition can be administered as part of a combination therapy, i.e. in combination with an additional agent or agents. Examples of materials that can be used as combination therapeutics with the peptides for treatment of autoimmune disease and demyelinating conditions as additional therapeutic agents include: an antibody or an antibody fragment that can bind specifically to an inflammatory molecule or an unwanted cytokine such as interleukin-6, interleukin-8, granulocyte macrophage colony stimulating factor, and tumor necrosis factor-$\alpha$; an enzyme inhibitor which can be a protein, such as $\alpha_1$-antitrypsin, or aprotinin; an enzyme inhibitor which can be a cyclooxygenase inhibitor; an engineered binding protein, for example, an engineered protein that is a protease inhibitor such an engineered inhibitor of kallikrein; an antibacterial agent, which can be an antibiotic such as amoxicillin, rifampicin, erythromycin; an antiviral agent, which can be a low molecular weight chemical, such as acyclovir; a steroid, for example a corticosteroid, or a sex steroid such as progesterone; a non-steroidal anti-inflammatory agent such as aspirin, ibuprofen, or acetaminophen; an anti-cancer agent such as methotrexate or adriamycin; or a cytokine.

An additional therapeutic agent can be a cytokine, which as used herein includes without limitation agents which are naturally occurring proteins or variants and which function as growth factors, lymphokines, interferons such as $\beta$-interferon, tumor necrosis factors, angiogenic or antiangiogenic factors, erythropoietins, thrombopoietins, interleukins, maturation factors, chemotactic proteins, or the like. Preferred combination therapeutic agents to be used with the composition of the invention and are $\beta$-interferon and/or Copaxone®. A therapeutic agent to be used with the composition of the invention can be an engineered binding protein, known to one of skill in the art of remodeling a protein that is covalently attached to a virion coat protein by virtue of genetic fusion (Ladner, R. et al., U.S. Pat. No. 5,233,409; Ladner, R. et al., U.S. Pat. No. 5,403,484), and can be made according to methods known in the art. A protein that binds any of a variety of other targets can be engineered and used in the present invention as a therapeutic agent in combination with a peptide of the invention.

An improvement in the symptoms as a result of such administration is noted by a reduction in symptoms such as the symptoms of MS noted herein. A therapeutically effective dosage preferably reduces frequency of MS episodes, and severity of symptoms such as fatigue, pain, and visual disturbances by at least about 20%, more preferably by at least about 40%, even more preferably by at least about 60%, and even still more preferably by at least about 80%, relative to untreated subjects. Cure of complete remission or improvement of symptoms can be noted by increased life span, elimination of relapsing episodes, and significantly improved overall health of the patient.

Another embodiment of the invention is a kit for assaying the binding of an analyte to an MHC protein associated with a demyelinating condition. This embodiment provides: a water-soluble MHC protein which is associated with a demyelinating condition and which has been recombinantly produced in a heterologous cell; a reaction chamber for containing the analyte and the MHC protein; and means for detecting binding of the analyte to the MHC protein. In a preferred embodiment, the MHC protein is produced in an invertebrate or a microbial cell, such as an insect cell or a yeast cell, and so is devoid of bound epitopes of human or mammalian origin, the bound peptide being in the antigen cleft, i.e., the MHC protein of the kit is "empty." Means for detecting binding of the analyte to the MHC protein can be radioactive, fluorimetric, ligand associating means such as biotinylated, chemiluminescent, or colorimetric means known to one of ordinary skill in the art. In a preferred embodiment of the kit, the MHC protein is a class II MHC HLA-DR1, -DR2, or -DR4 protein. Further, the kit can include also a reference material such as an autoantigenic peptide, such as a CII peptide, or a peptide derived from MBP, MOG, or a peptide from some other protein implicated in a demyelinating condition, such as a peptide comprising MBP residues at positions 85-99 (SEQ ID NO: 1).

The invention having now been fully described, embodiments are illustrated in the examples below, which are not intended to be further limiting. The contents of all cited patents and papers are hereby incorporated by reference herein.

EXAMPLES

The following materials and methods were used in the Examples below.

Methods for Protein Expression and Purification of Soluble HLA-DR2 Protein Molecules Soluble HLA-DR2 molecules were expressed in Drosophila S2 cells and purified as described (Kalandadze A. et al., J. Biol. Chem. 271:20156 (1996)). Cells were grown in roller bottles in ExCell 401 medium (JRH Biosciences, Lenexa, Kans.) supplemented with 2% fetal bovine serum (Sigma Chemicals, St. Louis, Mo.) at 26° C. Cells were harvested 4-5 days after induction by 1 mM $CuSO_4$. Supernatant from harvested cells was passed sequentially through Protein A, Protein G and Protein A-LB3.1 columns, followed by elution of the bound HLA-DR with 50 mM 3-[cyclohexylamino]-1-propanesulfonic acid and neutralized with 200 mM phosphate (pH 6.0). Proteins were concentrated on a Centriprep 10 membrane (Amicon, Beverly, Mass.).

Methods for Preparation of COP 1 Antigens

Cop 1 is a synthetic random copolymer prepared by polymerization of the N-carboxyanhydrides of L-tyrosine, γ-benzyl-L-glutamate, L-alanine and ε,N-trifluoroacetyl-L-lysine (Teitelbaum D, et al. Eur J Immunol 1:242, 1971). The end product is a mixture of acetate salts of random polypeptides. Copaxone® was obtained by prescription from a pharmacy. Biotinylation of Cop 1 was performed with excess N-hydroxysuccinimide biotin (Sigma) in dimethylsulfoxide (DMSO) as described (Fridkis-Hareli M. et al., Proc. Natl. Acad. Sci. U.S.A. 91:4872 (1994)). Unreacted biotin was removed by dialysis (Spectra/Por® membrane molecular weight cut-off 500); Spectrum Medical Industries, Laguna Hills, Calif.).

Method for Synthesis of Peptides

Peptides were synthesized on a 1 µmole scale using the Multipin Peptide Synthesis System (Chiron Mimotopes, Clayton, Australia) as 15-mers with a free amine at the N-terminus and a free acid at the C-terminus. Peptide synthesis was monitored by including two standard peptide sequences as controls, which were subjected to HPLC and mass spectroscopy analysis. The reference peptide MBP 85-99 (ENPVVHFFKNIVTPR; SEQ ID No.: 1), either unlabeled or with biotin linked to the N-terminus by the spacer serine-glycine-serine-glycine and free acid at C-terminus, was also included as a positive control for binding experiments. Pin peptides were lyophilized and resuspended at a concentration of 2 mg/ml in DMSO. These conditions allowed the majority of peptides to be completely solubilized.

Methods for Assays of Synthetic Peptide Binding to MHC class II HLA-DR2 Proteins The inhibitory activity of each test peptide is determined by the amount of inhibition of binding of biotin to HLA-DR2 molecules produced by the unlabeled test peptide, and compared to inhibition of binding produced by an equivalent molar amount of unlabeled MBP 85-99 or unlabeled Cop 1, and compared to binding in the absence of any inhibitor. A high inhibitory activity (expressed as percent inhibition) indicates that the test peptide inhibits an in vivo triggering of an autoimmune response associated with demyelinating conditions such as MS.

The solutions used in this assay are: binding buffer, 20 mM 2-[N-morpholino] ethanesulfonic acid (MES), 140 mM NaCl, and 0.05% $NaN_3$, pH 5.0, unless otherwise specified; PBS, 150 mM sodium chloride, 7.5 mM sodium phosphate, dibasic, and 2.5 mM sodium phosphate, monobasic, pH 7.2; TBS, 137 mM sodium chloride, 25 mM Tris pH 8.0, 2.7 mM potassium chloride; and TTBS, which is TBS with 0.05% Tween-20.

The preparation of microtiter plates for assay of peptide binding employed treated 96-well microtiter immunoassay plates (PRO-BIND™, Falcon, Lincoln Park, N.J.). Each well of the plates was coated with 1 µg/well affinity-purified LB3.1 monoclonal antibodies in PBS (100 µl per well) for 18 hrs at 4° C. The wells were then blocked with TBS/3% BSA for 1 hr at 37° C. and washed three times with TTBS. Prior to sample addition, 50 µl of TBS/1% BSA was added to each well.

Peptides to be tested are evaluated for inhibitory activity using inhibition reactions, which contained biotinylated Cop 1 or biotinylated MBP 85-99 at a final concentration of 1.5 µM and 0.13 µM, respectively, in 50 µl of binding buffer. This solution was coincubated for 40 hr at 37° C. with various amounts of each of the unlabeled test synthetic peptide (or as controls, Cop 1 or MBP 85-99), and with HLA-DR2 molecules.

Detection of class II MHC protein/peptide complexes was performed by measuring bound peptide-biotin, which was detected using streptavidin-conjugated alkaline phosphatase, as follows. Plates were washed three times with TTBS and incubated with 100 µl per well of streptavidin-conjugated alkaline phosphatase (diluted 1:3000, BioRad, Richmond, Calif.) for 1 hr at 37° C., followed by addition of p-nitrophenyl phosphate in triethanolamine buffer (BioRad). The absorbance at 410 nm was monitored by a microplate reader (model MR4000; Dynatech, Chantilly, Va.).

Methods for Assay of Inhibition of Antigen Presentation by Synthetic Peptides

Cell lines were constructed as follows. MBP 84-102-specific T cells were obtained from patients with relapsing-remitting MS carrying the MHC class II DR2 (8073, patient Ob (carrying the DRB1*1501 allele) and Hy1B, patient Hy (carrying the DRB1*1602 allele)) were transfected with TCR, into BW 58 TCR α⁻/β⁻ as recipient cells (Madsen, L. et al. Nature Genet. 23:343, 1999). Antigen presenting cells (APC) were L466 (L cells transfected with HLA-DR2 (DRB1*1501)) or MGAR (EBV-transformed B cells homozygous for DRB1*1501).

T-cell stimulation experiments were performed in a total volume of 200 µl in each well of a 96-well microtiter plate. Irradiated (3000 rad) APC ($2.5 \times 10^4$/well) were coincubated with the MBP 85-99 peptide (final concentration 12.5 µM) and with different concentrations of peptides for 2 hr at 37° C. After the incubation, T cells ($5 \times 10^4$/well) were added and the plates were further incubated for 24 hr at 37° C. Supernatants (30 µl) were removed, and were incubated with IL-2-dependent CTLL ($5 \times 10^4$/well) for 12 hr, followed by labeling with ³H-thymidine (1 µCi/well) for 12 hr. Plates were harvested and the radioactivity was monitored using a 1450 microbeta Plus liquids cintillation counter (Wallac, Gaithersburg, Md.).

Example 1

Criteria for Design of the Synthetic Peptides

A variety of peptide 15-mers were synthesized based on different amino acid sequences for conferring potential binding properties for the peptide binding groove of HLA-DR2. Each sequence was tested as part of the overall method of the design of the synthetic peptides (Table 1). Various combinations of glutamic acid (E), lysine (K) and alanine (A) were used at the N-terminus of the majority of the 82 peptides shown in Table 1. These residues were followed in most of the sequences by tyrosine (Y) at the location that corresponds to the P1 pocket of the bound peptide in complex with the MHC class II protein (referred to as the "P1 position"), and then by A in the subsequent positions (Fridkis-Hareli M. et al., J. Immunol. 162:4697 (1999)). In Table 1, the position in each synthetic peptide designed to occupy the P1 pocket is the fifth residue from the amino terminus, shown in bold. For certain synthetic peptides, additional peptides of closely related or almost identical sequence were designed, such that the Y in the P1 position of the sequence was replaced by other hydrophobic amino acids, such as phenylalanine (F), or valine (V).

In synthetic peptide group 1, the sequences were designed to have Y at the P1 position (corresponding to a valine, V, at residue number 89 which is at the P1 pocket in the protein complex with MBP 85-99 (Wucherpfennig K. W. et al., J. Exp. Med. 179:279 1994, also shown in the crystal structure of MBP 85-99 complexed with HLA-DR2; Smith K. J. et al., J. Exp. Med. 19:1511 (1998)).

In the synthetic peptides of group 2, A was designed to occupy the P1 pocket and Y was designed to occupy the P4 pocket (Table 1). The position in each synthetic peptide designed to occupy the P4 pocket is the eighth residue from the amino terminus in Table 1, and is shown in bold. This position corresponds to a phenylalanine, F, at residue number 92 of MBP 85-99 (SEQ ID NO: 1; Table 1).

In groups 3 and 4, synthetic peptides were designed that have Y at the positions in the sequence that occupy both the P1 and at P4 pockets, with A (group 3) or with K (group 4) at the P5 position (residue 93 in the MBP 85-99 peptide is a K). The P5 residue is located in a feature of the peptide that is a T-cell receptor (TCR) contact of the complex of the MHC class II HLA-DR2 protein with a bound peptide, and this residue is shown underlined in Table 1. The location of the TCR contact feature follows from the observation that binding of a K93A substitution in the MHC protein complex with the peptide altered the cytokine profile of MBP-reactive T-cell clones, reducing the secretion by the cells of IFN-γ to low levels (Ausubel L. J. et al., Proc. Natl. Acad. Sci. U.S.A. 93:15317 (1996); Ausubel L. J. et al., J. Immunol. 159: 2502 (1997); Anderson D. E. et al., J. Immunol. 159:1669 (1997)).

Synthetic peptides in group 5 were designed to have Y at the location that occupies the P1 pocket, with Y or A substituted for an F in the position corresponding to residue 91 of MBP. These peptides in group 5 were designed also to have a K at a location (the P5 position) corresponding to MBP residue 93 (Table 1).

Synthetic peptide #107 (SEQ ID NO: 69) in Table 1 has an amino acid sequence which is identical to that of MBP 85-99 except for a substitution of F to a Y in #107 peptide at residue 91 in MBP. This peptide was previously shown to induce proliferation of an MBP-reactive T-cell clone, such that induction was similar to that obtained with the original MBP 85-99 epitope (Ausubel L. J. et al., J. Immunol. 159: 2502 (1997)). Synthetic peptide #107 was used as a reference for characterization of the other group 5 synthetic peptides.

Synthetic peptides in group 6, with two exceptions, were designed to have a V in the amino acid sequence residue that occupies the P1 pocket. The exceptions include peptide #117 (SEQ ID NO: 80), which was designed to have a Y, and peptide #119 (SEQ ID NO: 82) which has an A, at the residue designed to occupy the P1 pocket in the sequence of each peptide (Table 1).

The amino acid sequences of the group of designed synthetic peptides further included one or more E and/or K residues, consistent with previous data on sequences of MHC class II protein binding motifs, and to improve the solubility of the synthetic peptides.

Additional peptides were synthesized to test whether a hydrophobic residue is essential to inhibitory activity in the amino acid position 5 which interacts with the P1 pocket; to vary hydrophobic residue sizes; and to test the relationship between amino acid side group structure and effect on inhibitory function of other positions in the peptides.

Example 2

Inhibition of Cop 1 and MBP 85-99 Binding to HLA-DR2 Molecules by the Synthetic Peptides To examine whether the synthetic peptides competed either Cop 1, or with the immunodominant high affinity epitope peptide MBP 85-99 (SEQ ID NO: 1) for binding to HLA-DR2 molecules, competitive binding assays were carried out with biotinylated Cop 1 or with biotinylated MBP 85-99 as a test compound, to measure relative affinity of each of the unsubstituted (unbiotinylated and otherwise unlabeled) inhibitors (Cop 1, MBP 85-99 and each of the synthetic peptides).

The results of such assays using biotinylated Cop 1 as the test compound showed that unsubstituted Cop 1 or MBP 85-99 (SEQ ID NO: 1) inhibited binding of biotinylated Cop 1 to recombinant HLA-DR2 protein to a greater extent than most of the designed synthetic peptides in groups 1-6 (Table 1). Peptides in groups 1-3 and in group 6 were poor competitors of Cop 1 binding (Table 1).

Inhibition of binding of biotinylated Cop 1 (panel A) or biotinylated MBP 85-99 (panel B) to HLA-DR2 molecules by each of several examples of the synthetic peptides is shown in FIG. 1. Recombinant HLA-DR2 molecules were incubated with 1.5 μM of biotinylated Cop 1 or 0.13 μM of biotinylated MBP 85-99 alone, or further in the presence of unlabeled competitors at the range of concentrations shown in the figure, and the signals at 410 nm were measured. (Control wells of the ELISA plate without competitor had an absorbance of 0.90-0.95, and the background was 0.12.)

Surprisingly, several synthetic peptides in group 4 (containing Y at locations that occupy P1 and P4 pockets of the MHC class II protein) inhibited binding of biotinylated Cop 1 to HLA-DR2 better than either Cop 1 or the MBP 85-99 peptide, with peptides #100-#103 (SEQ ID NOS: 64-67, respectively) being most effective (Table 1, FIG. 1A).

Several synthetic peptides in group 4 inhibited binding of biotinylated Cop 1 better than most of the other peptides including MBP 85-99, which in FIG. 1 and Table 1 is denoted by the numeral 3 (SEQ ID NO: 1), as is shown in FIG. 1A. Further, synthetic peptide #101 (open triangles; SEQ ID NO: 65), inhibited binding of biotinylated Cop 1 to MHC class II DR2 protein to a greater extent and at lower concentration than MBP 85-99 (closed squares; SEQ ID NO: 1).

Several synthetic peptides, for example, #94 (open squares; SEQ ID NO: 60), #96 (open circles; SEQ ID NO: 62), #99 (open triangles; SEQ ID NO: 63) and #107 (closed triangles; SEQ ID NO: 69), were more effective than Cop 1 (closed circles) as inhibitors of binding of biotinylated MBP 85-99 peptide to MHC class II DR2 protein, as shown in FIG. 1B.

The results of assays using biotinylated MBP 85-89 as the test compound showed that several peptides inhibited binding of the biotinylated MBP 85-99 peptide to HLA-DR2 molecules very efficiently. The best inhibitors were: unlabeled MBP peptide; synthetic peptide #107 (group 5; SEQ ID NO: 69), which is an analog of the MBP 85-99 with a substitution of F to Y at the location corresponding to residue 91 in the MBP 85-99 peptide; and the following synthetic peptides of group 4: #94 (SEQ ID NO: 60), #96 (SEQ ID NO: 62), #99 (SEQ ID NO: 63) and #101 (SEQ ID NO: 65), containing Y at both positions corresponding to residue numbers 89 and 92 of MBP (the P1 and P4 pockets) and K at both positions corresponding to MBP residue numbers 90 and 93 (Table 1, FIG. 1B). Surprisingly, Cop 1 inhibited binding of the biotinylated MBP peptide 85-99 test compound less efficiently than these particular synthetic peptides (Table 1).

Example 3

Synthetic Peptide Inhibition of Proliferation and IL-2 Secretion by HLA-DR2 Restricted MBP 85-99-Specific T Cells To determine whether the synthetic peptides that bind to MS-associated HLA-DR2 molecules would inhibit presentation of the MBP 85-99 peptide to HLA-DR2-restricted T cells, MBP 84-102-specific T cell transfectants were examined. These T cells were previously generated by transfection of BW 58 TCR α$^-$/β$^-$ cells with DNA encoding a TCR. The TCR gene was obtained from patients with relapsing-remitting MS, the patients carrying DR2 alleles 8073, patient Ob (DRB1*1501) and Hy1B, patient Hy (DRB1*1602); (Madsen L. S. et al., Nat. Genet. 23:343 (1999). Irradiated APC (L466 or MGAR) were incubated with MBP 85-99 and the synthetic peptides for 2 hrs, then T cells were added for 24 hrs. Supernatants were tested for cell proliferation, and for IL-2 secretion by ability of samples to stimulate growth of IL-2-dependent CTLL.

Inhibition in the presence of the synthetic peptides of proliferation of HLA-DR2-restricted MBP 84-102-specific T cell transfectants Hy1B (FIG. 2A) and 8073 (FIG. 2B) was demonstrated with each of the indicated peptides. Irradiated cells MGAR (FIG. 2A) or L466 (FIG. 2B) were coincubated in duplicate with MBP 85-99 (final peptide concentration 12.5 μM). Then the synthetic peptide or Cop 1 was added at the indicated final concentration, and the mixtures were incubated for 2 hr at 37° C., followed by addition of T cells Hy1B (FIG. 2A) or 8073 (FIG. 2B), and incubation for 24 hr at 37° C. Supernatants (30 μl) were incubated with IL-2-dependent CTLL, followed by labeling with $^3$H-thymidine (1 μCi/well) for 12 hr to measure proliferation.

Figure 2:
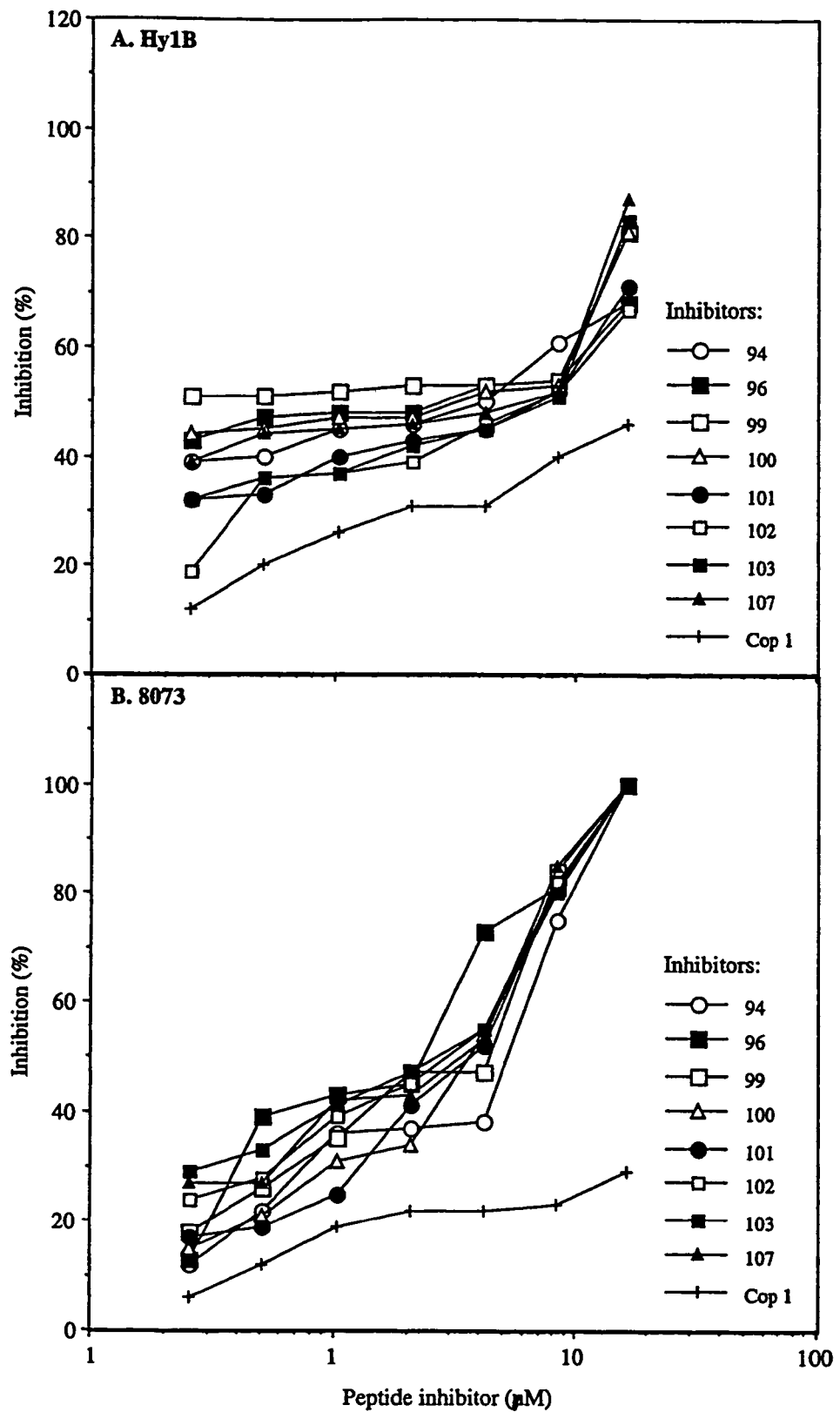
FIG. 2 is a line graph that shows the inhibition of proliferation of HLA-DR2 restricted MBP 84-102-specific T cell line transfectants Hy1B (FIG. 2A) and 8073 (FIG. 2B) as a function of the concentration of Cop 1 or each of synthetic peptides: #94 (SEQ ID NO: 60); #96 (SEQ ID NO: 62); #99 (SEQ ID NO: 63); #100-#103 (SEQ ID NOs: 64-67, respectively); and #107 (SEQ ID NO: 69).

The data show that several of the synthetic peptides inhibited proliferation of MBP 85-99-reactive Hy1B T cells, using HLA-DR2-expressing MGAR cells as APC (Table 1, FIG. 2A). The synthetic peptides that were most inhibitory included #94 (SEQ ID NO: 60), #96 (SEQ ID NO: 62), #99 (SEQ ID NO: 63), #100 (SEQ ID NO: 64), #101 (SEQ ID NO: 65), #102 (SEQ ID NO: 66), #103 (SEQ ID NO: 67) and #107 (SEQ ID NO: 69), for inhibition of T-cell presentation both to Hy1B and to 8073 cells.

Synthetic peptides which inhibited binding of biotinylated MBP 85-99 or Cop 1 to HLA-DR2 molecules (FIG. 1 and Table 1) were here found to also be good inhibitors of MBP 85-99-reactive Hy1B cells (FIG. 2A). Synthetic peptides #94 (SEQ ID NO: 60), #96 (SEQ ID NO: 62) and #99 (SEQ ID NO: 63) had K at both residues equivalent to residues 90 and 93 (of the sequence of MBP), whereas synthetic peptide #100 (SEQ ID NO: 64), #101 (SEQ ID NO: 65) and #102 (SEQ ID NO: 66) had K at the residues corresponding to 88 and 93 (the P−1 and P5 locations, respectively, in MBP 85-99; Table 1). When 8073 T-cell transfectants and L466 APC were used, most of the active inhibitory synthetic peptides showed higher levels of inhibition compared to their activity as determined by testing with Hy1B cells.

In contrast, Cop 1 had little effect on MBP-specific T-cell response, when used at a molar concentration similar to that at which the synthetic peptides were tested, with Hyl B cells (Table 1, FIG. 2A), and with 8073 cells (FIG. 2B).

Without being limited to a particular theory or mechanism of action, these data indicate that the peptides herein may be advantageous as therapeutic agents, for example, for co-administration with other agents such as α-interferon or CoP−1, the combination more able to inhibit various aspects of the function of MHC class II molecules, or for administration in dosages at lower molar quantities than Cop 1.

Example 4

Requirement for a Hydrophobic Amino Acid Residue at the P1 Site

A variety of synthetic peptides were designed, synthesized, and tested herein for ability to compete with binding of biotinylated MBP 85-99 (SEQ ID NO: 1) to MHC class II HLA-DR2 molecules. Based on the results with the best peptides above, and in order to further elucidate the requirements of size, shape, charge and hydrophobicity in the interactions with this protein, additional peptides were designed, synthesized and tested.

Peptide #1 in FIG. 3 (identical to peptide #101 in Table 1; SEQ ID NO: 65) was used as a template for design of additional related peptides, the related peptides designed to have glutamic acid (E) at the P1 position (peptides #4 and #6; SEQ ID NOs: 92 and 94, respectively). Peptide #6 further contains proline residues located at positions near to each of the N- and C-termini (at each of positions 3 and 14 within the 15-mer peptide), similar to positions of prolines in MBP85-99 (SEQ ID NO: 1). The peptides having E at the P1 position were used to determine whether a hydrophobic amino acid is optimal or required at this position in the sequence, for the desirable inhibitory activity of the peptide.

Figure 3A:
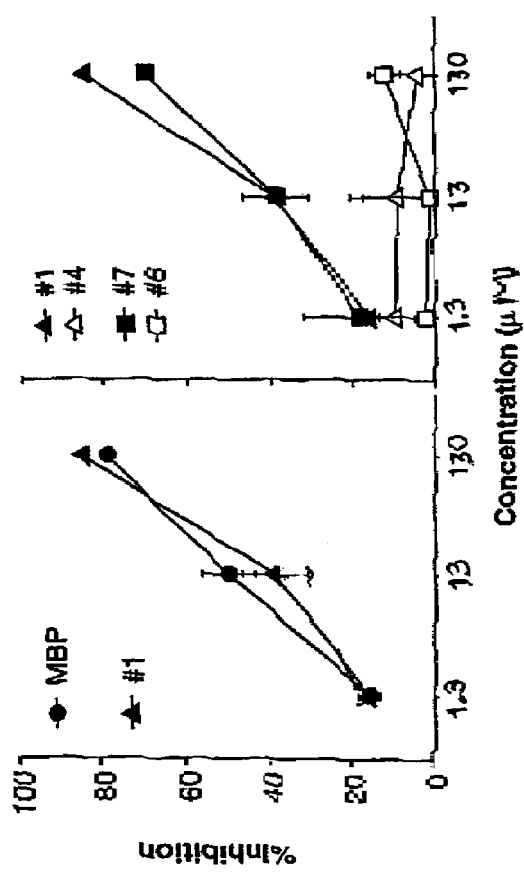
FIG. 3A on the left is a line graph that shows the inhibition of biotinylated MBP 85-99 by each of MBP 85-99 (SEQ ID NO: 1), or #101 (designated #1 in the FIG., solid triangles; SEQ ID NO: 65)
Figure 3B:
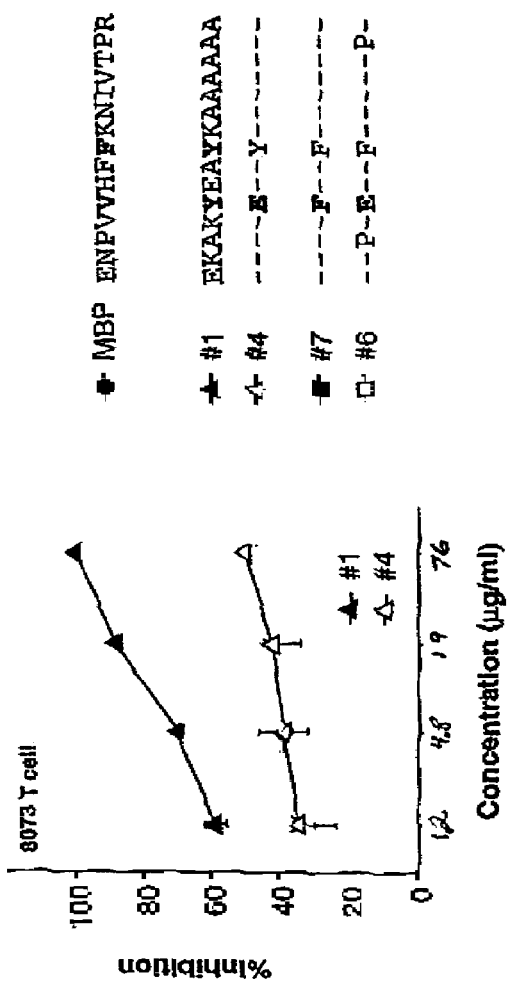
FIG. 3B is a line graph that shows the inhibition of proliferation of HLA-DR2 restricted MBP 84-102-specific T cell transfectant 8073 as a function of the concentration each of synthetic peptides: #101 (designated #1 in the FIG., solid triangles; SEQ ID NO: 65); and #4 (SEQ ID NO: 92).

FIG. 3A confirms data shown above, indicating that peptide #1 (SEQ ID NO: 65) is at least as effective as MBP 85-99 in ability to inhibit binding of biotinylated MBP 85-99 (SEQ ID NO:1) to HLA-DR2 molecules. Replacement of the hydrophobic residue tyrosine (Y) at the P1 position at the residue corresponding to position 89 in MBP 85-99 (position number 5 in each of the peptides synthesized herein) with E, as in the sequences of peptides #4 and #6, however, reduces or eliminates inhibitory ability, indicating that high affinity to the MHC class II HLA-DR2 is been substantially related to having a hydrophobic residue at this position. FIG. 3B further indicates that ability to inhibit proliferation of HLA-DR2 restricted MBP 84-102-specific T cell line transfectant 8073 of peptide #1 (SEQ ID NO: 65) is substantially reduced by replacement of Y by E at the P1 position, by comparison to the data obtained using peptide #4 (SEQ ID NO: 92).

Example 5

Testing the Relative Sizes of Hydrophobic Amino Acids for Fit to the P1 Pocket

A set of derivatives of peptide #2 (SEQ ID NO: 85) were synthesized, so that the Y in position 5 of that peptide, corresponding to the residue at position 89 of MBP 85-99 that interacts with the P1 pocket of MHC class II, was replaced by each of phenylalanine (F; peptide #3; SEQ ID NO:91) and valine (V; peptide #5; SEQ ID NO:93). Peptide #2 shares sequence features with each of peptide #1 and MBP 85-99, having prolines (P) at each of positions 3 and 14 in the 15-mer peptide sequence.

Figures 4A, 4B:
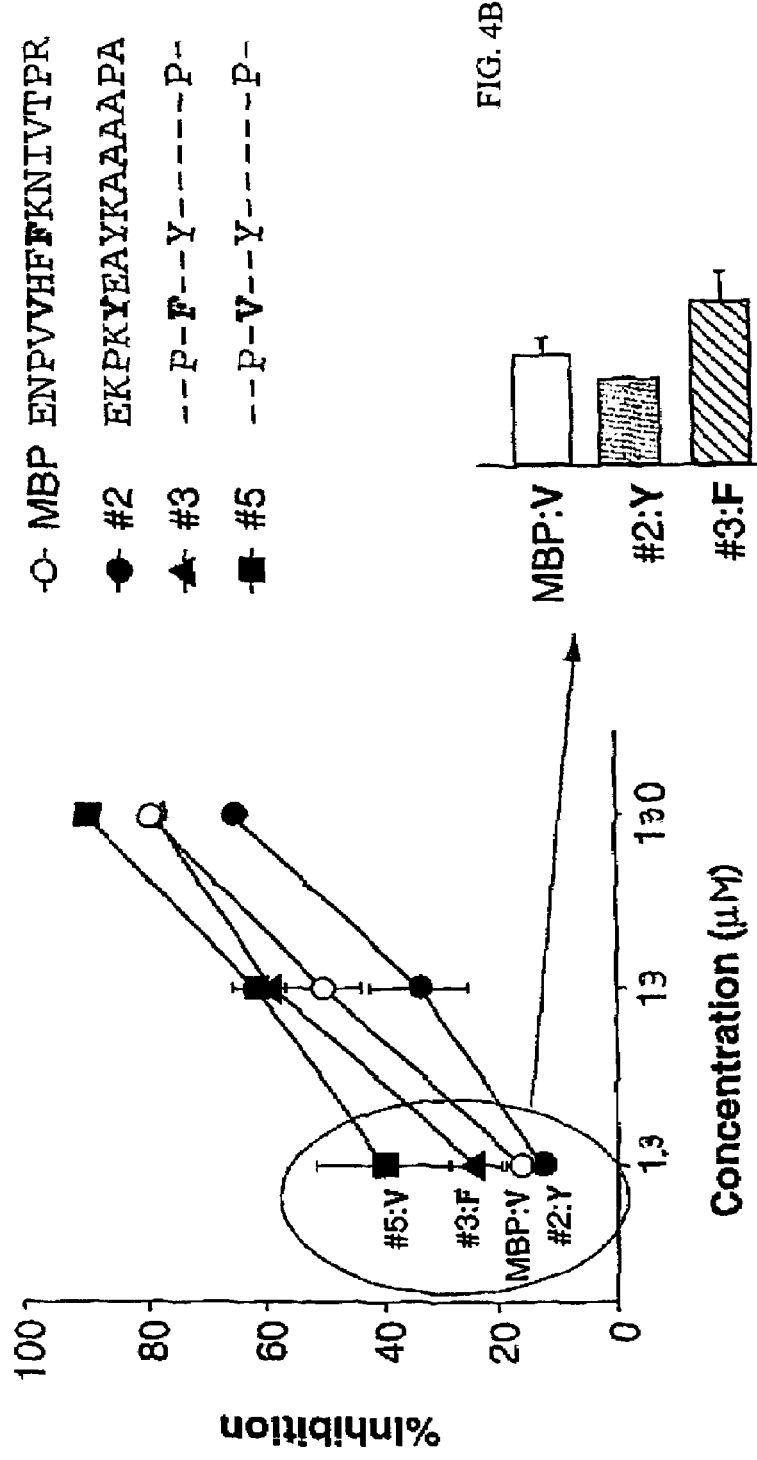
FIG. 4A is a line graph that shows the inhibition of biotinylated MBP 85-99 binding to HLA-DR2 molecules as a function of concentration of each of unlabeled peptides MBP 85-99 (SEQ ID NO: 1); #2 (SEQ ID NO: 85); #3 (SEQ ID NO: 91); and #5 (SEQ ID NO: 93).
FIG. 4B is a bar graph comparing the data obtained for these peptides at a concentration of 1.3 .mu.M, and shows that for peptides that are otherwise identical in sequence, hydrophobic residues at the P1 position that are less bulky, such as valine (V) result in a peptide that is more inhibitory, compared to residues that are more bulky such as tyrosine (Y).

FIG. 4A shows the extent of inhibition of biotinylated MBP 85-99 binding to HLA-DR2 molecules as a function of concentration of each of unlabeled peptides MBP 85-99 (SEQ ID NO: 1); #2 (SEQ ID NO: 85); #3 (SEQ ID NO: 91); and #5 (SEQ ID NO: 93). From these data it can be seen that the valine replacement found in peptide #5 (SEQ ID NO:93) yields a sequence with the greatest ability among peptides in this example to inhibit binding of MBP 85-99 to HLA-DR2 molecules. FIG. 4B displays data for each of the tested peptides at the 1.3 µM concentration. The data show that for peptides that are otherwise identical in sequence, having a hydrophobic residue that is less bulky, i.e., valine (V) at position 5 corresponding to MBP position 89, that interacts in the P1 pocket, as in peptide #5 (SEQ ID NO: 93), results in a peptide that is more inhibitory than are otherwise identical peptides having a bulkier residue (tyrosine, Y, or phenylalamine, F) at the same position in the peptide.

Further, the least inhibitory peptide among the three peptides each having a hydrophobic residue of different size was peptide #2, which carries tyrosine (Y). The Y side group is considered to be the largest among amino acids, Y, F and V. These data indicate that the smaller hydrophobic side chain of V results in greater inhibitory activity than otherwise identical 15-mer peptides with amino acid sequences having larger hydrophobic side chains (F and Y). Thus V in position number 5 provides a 15-mer peptide having the best fit with the P1 pocket of HLA-DR2 molecules.

Example 6

Effect of a Charged Amino Acid in the P–3 Position

Peptide derivatives were synthesized having replacements of lysine (K), a positively charged amino acid as is found in the amino acid sequence peptide #3, to a neutral amino acid, in position 2 of the 15-mers, corresponding to the P–3 position as relates to the residue at position 5 of MBP 85-99 that interacts with the P1 pocket of HLA-DR2 molecules. These replacements were synthesized based on the observation that MBP 85-99 (SEQ ID NO: 1) has a neutral amino acid (asparagine, N) at that location.

The data in FIG. 5A show inhibition of binding of biotinylated MBP 85-99 to HLA-DR2 molecules peptides at a concentration of 1.3 µM for each of unlabeled peptides MBP 85-99 (SEQ ID NO: 1); #3 (SEQ ID NO: 91); #5 (SEQ ID NO: 93); #13 (SEQ ID NO: 98); and #14 (SEQ ID NO: 99). The data suggest that a peptide with a neutral amino acid at this position has inhibitory ability that is at least as good as that having a charged amino acid at this position.

However, data shown in FIG. 5B, in which the inhibition of HLA-DR2 restricted MBP 84-102-specific T cell line transfectant 8073 as a function of the concentration of each of synthetic peptides: #3 (SEQ ID NO: 91); #5 (SEQ ID NO: 93); #13 (SEQ ID NO: 98); and #14 (SEQ ID NO: 99) further indicate that substitution of an A residue at the P–3 position (peptide #13) for a K residue (#3) reduces the inhibitory activity for T cell proliferation of these peptides.

Example 7

Figure 6A:
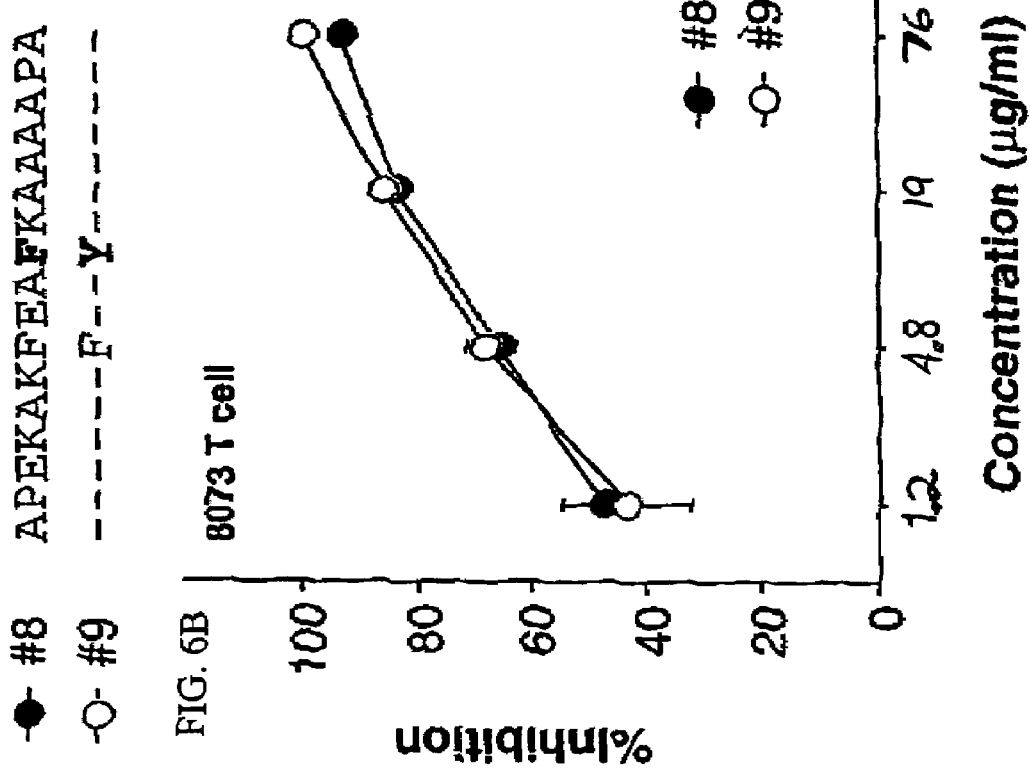
FIG. 6A is a line graph that shows the inhibition of biotinylated MBP 85-99 binding to HLA-DR2 molecules as a function of concentration of unlabeled synthetic peptides: #8 (SEQ ID NO: 96); and #9 (SEQ ID NO: 97).
Figure 6B:
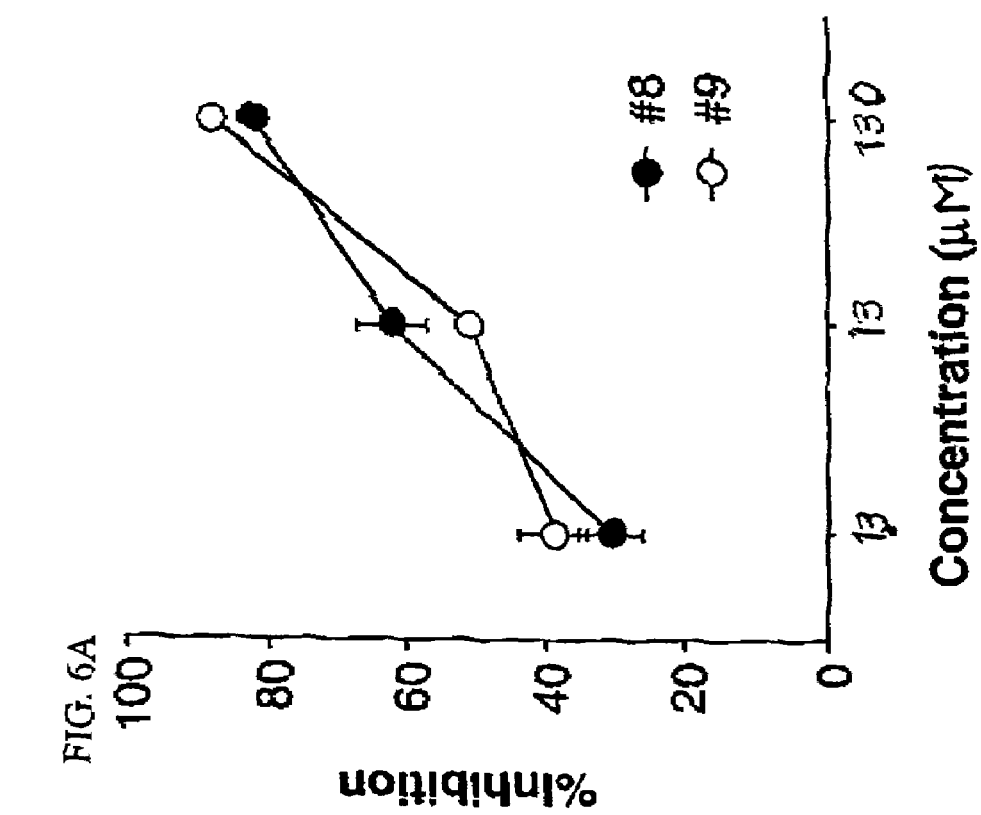
FIG. 6B is a line graph that shows the inhibition of proliferation of HLA-DR2 restricted MBP 84-102-specific T cell transfectant 8073 as a function of the concentration of each of synthetic peptides #8 (SEQ ID NO: 96); and #9 (SEQ ID NO: 97). The data show that phenylalanine (F) and tyrosine (Y) at the P4 position are equally effective with respect to inhibitory activity.

Comparison of Hydrophobic Residues Tyrosine and Phenylalanine at the P4 Position FIG. 6A shows the inhibition of biotinylated MBP 85-99 (SEQ ID NO: 1) binding to HLA-DR2 molecules as a function of concentration of unlabeled synthetic peptides: #8 (SEQ ID NO: 96); and #9 (SEQ ID NO: 97). FIG. 6B shows the inhibition of HLA-DR2 restricted MBP 84-102-specific T cell transfectant 8073 as a function of the concentration of each of synthetic peptides #8 (SEQ ID NO: 96); and #9 (SEQ ID NO: 97).

The data show that phenylalanine (F) and tyrosine (Y), at the P4 position in the peptide, are about equally effective with respect to inhibitory activity of the peptide, both for competition of MBP 85-99 binding to HLA-DR2 molecules, and for inhibition of T cell proliferation.

Example 8

Figure 7:
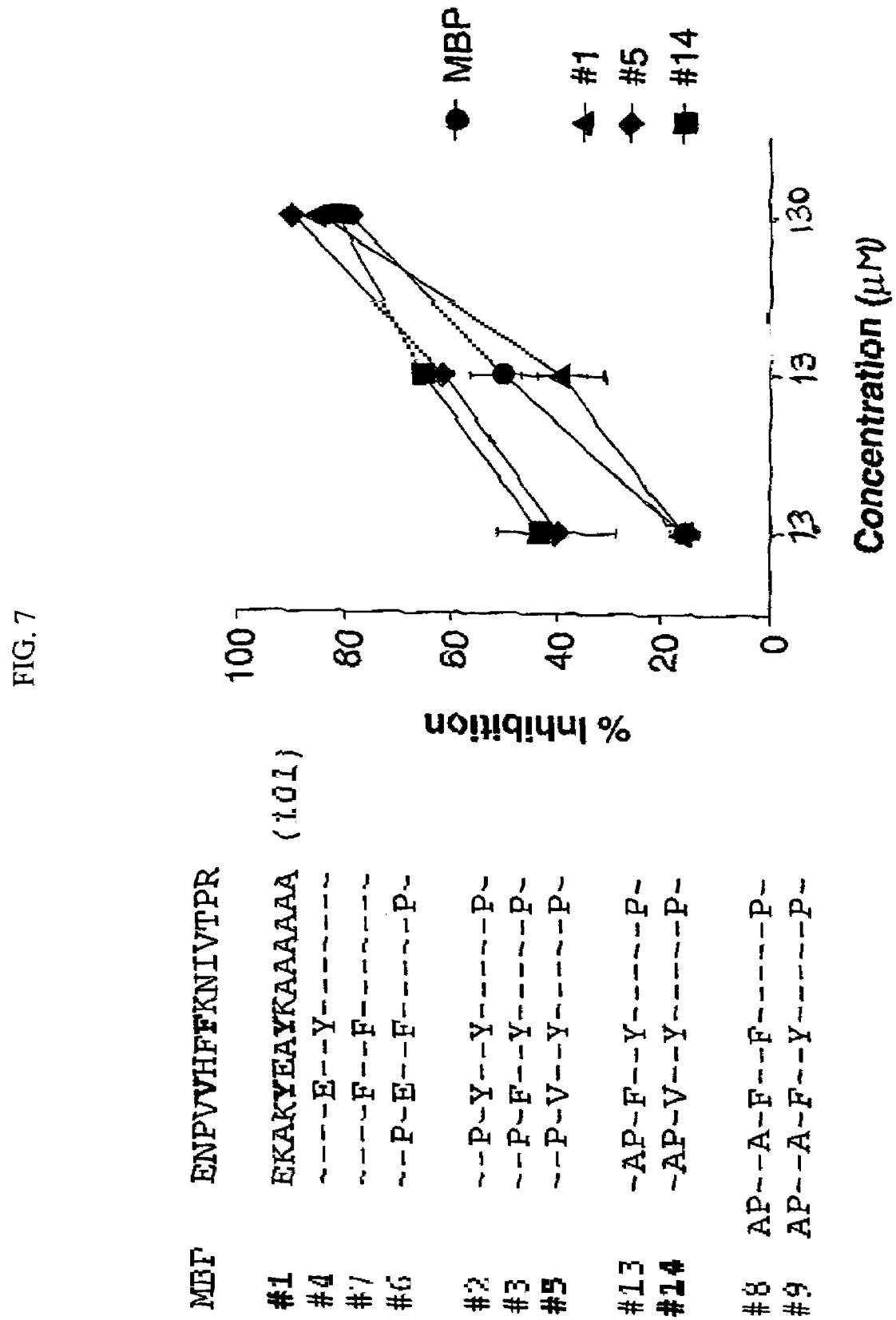
FIG. 7 is a line graph that shows the inhibition of biotinylated MBP 85-99 binding to HLA-DR2 molecules as a function of concentration of each of the synthetic peptides: MBP 85-99 (SEQ ID NO: 1); #101 (designated #1 in the FIG., solid triangles; SEQ ID NO: 65); #5 (SEQ ID NO: 93); and #14 (SEQ ID NO: 99). Peptides #5 and #14, having V at the P1 position, Y and the P4 position, and either K or A at the P–3 position, are equally effective inhibitors.

Comparison of Three Peptides for Affinity to HLA-DR2 Molecules by Competition with Biotinylated MBP 85-99, and Inhibition of Proliferation of T Cells Peptides #1, #5 and #14 (SEQ ID NOs: 65, 93, and 99, respectively) were compared in a single assay with unlabeled MBP 85-99 (SEQ ID NO: 1), by the two criteria of inhibitory activity used in the Examples herein. The data in FIG. 7 show that, by the criterion of inhibition of biotinylated MBP 85-99 (SEQ ID NO: 1) binding to HLA-DR2 molecules as a function of concentration, each of peptides #5 and #14 were at least as effective as inhibitors of biotinylated MBP binding to HLA-DR2 molecules, and possibly more effective, than MBP 85-99. Peptides #5 and #14 each have V at the P1 position and Y at the P4 position, and differ in having either K or A at the P−3 position, respectively, and were found to be equally effective inhibitors.

Figure 8:
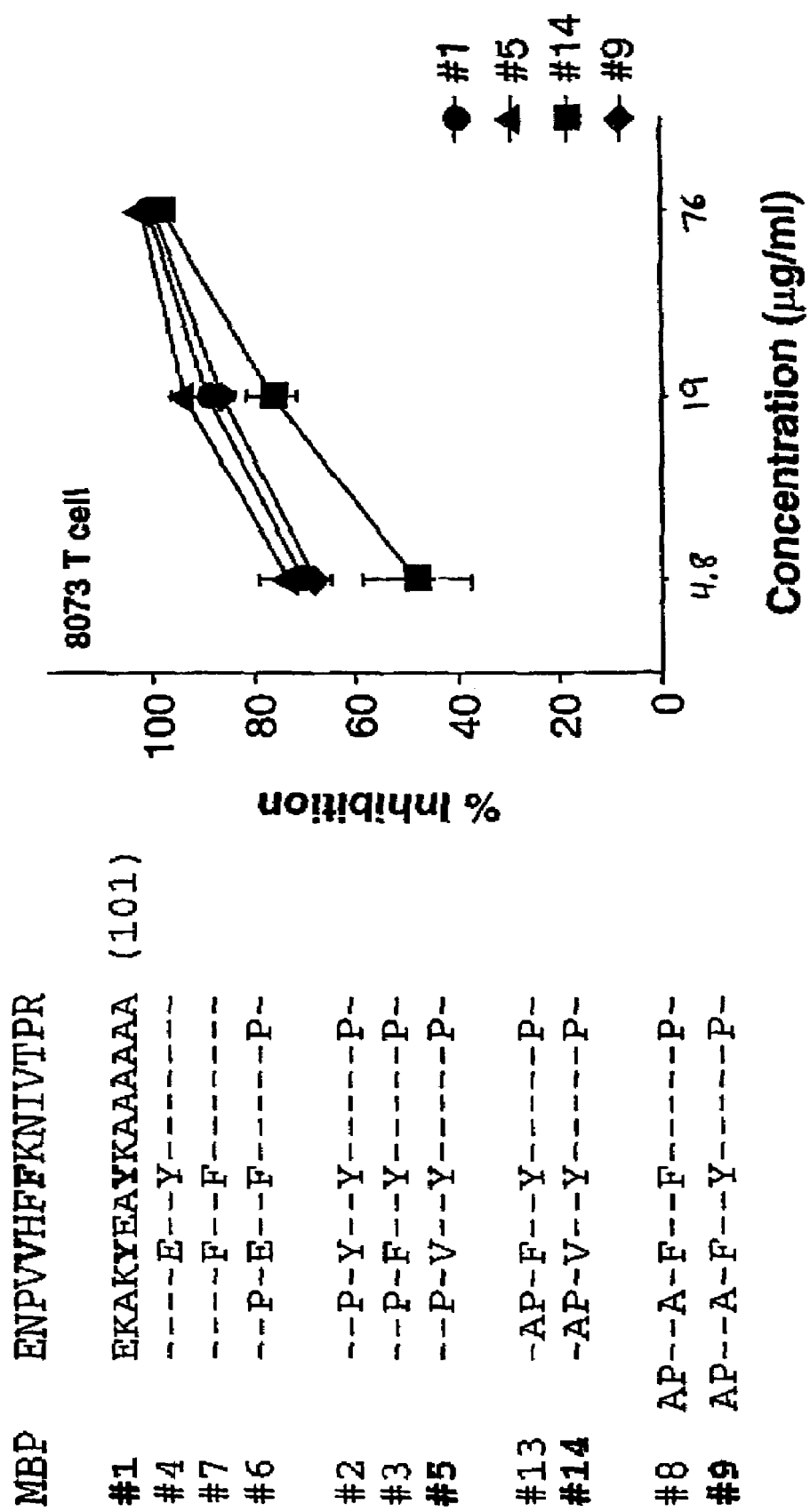
FIG. 8 is a line graph that shows the inhibition of proliferation of HLA-DR2 restricted MBP 84-102-specific T cell transfectant 8073 as a function of the concentration of each of synthetic peptides #1 (SEQ ID NO: 65); #5 (SEQ ID NO: 93); #9 (SEQ ID NO: 97); and #14 (SEQ ID NO: 99). All synthetic peptides show better inhibitory activity than Cop 1.

Further, FIG. 8 shows that, by the criterion of inhibition of proliferation of HLA-DR2 restricted MBP 84-102-specific T cell line transfectant 8073, that peptides #1, #5 and #9 were more effective than #14. Peptide #14 (SEQ ID NO: 99) has an F rather than the more favorable V in the P1 position, and is longer in sequence, having a length of 17 amino acids, confirming the value of V at the P1 position.

Assays using inhibition of proliferation of 2E12 T cells, another HLA-DR2 restricted MBP 84-102-specific T cell line, supported findings obtained with the transfectant 8073 cell line. These assays show that that peptides #1 and #5, having either an F or a V at the position corresponding to that of position 89 of MBP 85-99 and interacting with the P1 pocket of HLA-DR2 molecules, are the most successful inhibitors.

Example 9

Derivatives and Oligomers of Peptides

Peptides compositions described herein can be arrayed in oligomers or polymers having the peptide amino acid sequence as a monomer, the sequence being repeated in a linear fashion as a homopolymer of the same sequence, or as a heteropolymer including an amino acid sequence of more than one peptide sequence. The peptide amino acid sequences can be separated by a short flexible linker, for example, comprising small uncharged amino acids. Further, an amino acid sequence of a peptide may be derivatized, for example, containing amino acid analogs such as D-amino acids or peptidomimetic bonds. Such amino acid oligomer and polymer sequences, and chemical derivatives thereof, are within embodiments of the present invention, and can be produced synthetically or by production in recombinant organisms carrying a nucleic acid encoding the polymer sequence.

TABLE 1

Affinity of the binding of the synthetic peptides to HLA-DR2 molecules, and inhibition of HLA-DR2-restricted MBP 84-102-specific T-cell clones

| Group | #[a] | (SEQ ID NO) | Amino acid sequence | $IC_{50}$ (μM)[b] vs. biotinylated MBP 85-99 | $IC_{50}$ (μM)[b] vs. biotinylated Cop 1 | Inhibition of IL-2 production (%)[c] Hy1B |
|---|---|---|---|---|---|---|
| Ref. | Cop 1 | NA[d] | poly (Y,E,A,K) | 100 | 7 | 46 |
| Ref. | MBP 85-99 | (1) | ENPVVHFFKNIVTPR | 7 | 28 | NA[d] |
| 1. | 37 | (2) | AKKEYAAAAAAAAAA | >1000 | >1000 | 5 |
|  | 38 | (3) | AKEEYAAAAAAAAAA | >1000 | >1000 | 17 |
|  | 39 | (4) | AKEAYAAAAAAAAAA | >1000 | >1000 | 32 |
|  | 40 | (5) | AEKEYAAAAAAAAAA | >1000 | >1000 | 22 |
|  | 41 | (6) | EKKAYAAAAAAAAAA | >1000 | >1000 | 7 |
|  | 42 | (7) | KEEYAAAAAAAAAAA | >1000 | >1000 | 49 |
|  | 43 | (8) | AEKAYAAAAAAAAAA | >1000 | >1000 | 0 |
|  | 44 | (9) | EKAAYAAAAAAAAAA | >1000 | >1000 | 0 |
|  | 105 | (10) | EEKAYAAAAAAAAAA | >1000 | >1000 | 36 |
| 2. | 45 | (11) | AKEAAAAYAAAAAAA | 95 | >150 | 0 |
|  | 46 | (12) | EKEAAAAYAAAAAAA | >1000 | >1000 | 0 |
|  | 47 | (13) | KEKAAAAYAAAAAAA | >1000 | >1000 | 13 |
|  | 48 | (14) | AKAEAAAYAAAAAAA | >1000 | >1000 | 27 |
|  | 49 | (15) | AEKAAAAYAAAAAAA | >1000 | >1000 | 36 |
|  | 50 | (16) | AKKAAEAYAAAAAAA | 10 | 40 | 22 |
|  | 51 | (17) | AKAAAAEYAAAAAAA | >1000 | >1000 | 3 |
| 3. | 52 | (18) | AEKAYAAYAAAAAAA | 150 | >150 | 20 |
|  | 53 | (19) | AEEAYKAYAAAAAAA | 150 | >150 | 13 |
|  | 54 | (20) | AEKKYAAYAAAAAAA | >1000 | >1000 | 38 |
|  | 55 | (21) | AAEKYAAYAAAAAAA | >1000 | >1000 | 30 |
|  | 56 | (22) | AEEKYAAYAAAAAAA | >1000 | >1000 | 16 |
|  | 57 | (23) | AKEAYAAYAAAAAAA | >1000 | >1000 | 0 |
|  | 58 | (24) | AAKEYAAYAAAAAAA | >1000 | >1000 | 16 |
|  | 59 | (25) | AKAEYAAYAAAAAAA | >1000 | >1000 | 29 |
|  | 60 | (26) | AEAKYAAYAAAAAAA | >1000 | >1000 | 0 |
|  | 61 | (27) | AAEEYKAYAAAAAAA | >1000 | >1000 | 35 |
|  | 62 | (28) | AKEEYAAYAAAAAAA | >1000 | >1000 | 22 |
|  | 63 | (29) | AKEKYAAYAAAAAAA | >1000 | >1000 | 29 |
|  | 64 | (30) | AKAAYEAYAAAAAAA | >1000 | >1000 | 18 |
|  | 65 | (31) | AAKAYEAYAAAAAAA | >1000 | >1000 | 22 |
|  | 66 | (32) | AEAEYKAYAAAAAAA | >1000 | >1000 | 43 |
|  | 67 | (33) | AEAKYEAYAAAAAAA | >1000 | >1000 | 41 |
|  | 68 | (34) | AAKKYEAYAAAAAAA | >1000 | >1000 | 41 |
|  | 69 | (35) | AAEKYEAYAAAAAAA | >1000 | >1000 | 45 |
|  | 70 | (36) | AAAEYKAYAAAAAAA | >1000 | >1000 | 24 |

TABLE 1-continued

Affinity of the binding of the synthetic peptides to HLA-DR2 molecules, and inhibition of HLA-DR2-restricted MBP 84-102-specific T-cell clones

| Group | #[a] | (SEQ ID NO) | Amino acid sequence | IC$_{50}$(µM)[b] vs. biotinylated MBP 85-99 | IC$_{50}$(µM)[b] vs. biotinylated Cop 1 | Inhibition of IL-2 production (%)[c] Hy1B |
|---|---|---|---|---|---|---|
|  | 71 | (37) | EAEKYAAYAAAAAAA | >1000 | >1000 | 25 |
|  | 72 | (38) | EKAEYAAYAAAAAAA | >1000 | >1000 | 39 |
|  | 73 | (39) | EKEAYAAYAAAAAAA | >1000 | >1000 | 23 |
|  | 74 | (40) | EAKEYAAYAAAAAAA | >1000 | >1000 | 22 |
|  | 75 | (41) | EAKAYAAYAAAAAAA | >1000 | >1000 | 19 |
| 4. | 76 | (42) | AAAEYAAYKAAAAAA | >1000 | >1000 | 52 |
|  | 77 | (43) | AAEKYAAYKAAAAAA | >1000 | >1000 | 61 |
|  | 78 | (44) | AKEAYAAYKAAAAAA | >1000 | >1000 | 59 |
|  | 79 | (45) | AEAKYAAYKAAAAAA | >1000 | >1000 | 50 |
|  | 80 | (46) | AEEAYAAYKAAAAAA | >1000 | >1000 | 30 |
|  | 81 | (47) | AKAEYAAYKAAAAAA | >1000 | >1000 | 28 |
|  | 82 | (48) | AKEEYAAYKAAAAAA | >1000 | >1000 | 47 |
|  | 83 | (49) | AEEKYAAYKAAAAAA | >1000 | >1000 | 43 |
|  | 84 | (50) | AAKEYAAYKAAAAAA | >1000 | >1000 | 42 |
|  | 85 | (51) | EAAKYAAYKAAAAAA | >1000 | >1000 | 25 |
|  | 86 | (52) | EAKAYAAYKAAAAAA | >1000 | >1000 | 29 |
|  | 87 | (53) | EKAAYAAYKAAAAAA | >1000 | >1000 | 40 |
|  | 88 | (54) | EAEAYAAYKAAAAAA | >1000 | >1000 | 55 |
|  | 89 | (55) | EAAEYAAYKAAAAAA | >1000 | >1000 | 41 |
|  | 90 | (56) | EEAAYAAYKAAAAAA | >1000 | >1000 | 22 |
|  | 91 | (57) | EEAKYAAYKAAAAAA | >1000 | >1000 | 54 |
|  | 92 | (58) | EKEAYAAYKAAAAAA | >1000 | >1000 | 42 |
|  | 93 | (59) | AAKAYEAYKAAAAAA | 8 | >150 | 48 |
|  | 94 | (60) | AAEAYKAYKAAAAAA | 3 | >150 | 50 |
|  | 95 | (61) | EAKAYEAYKAAAAAA | 40 | >1000 | 47 |
|  | 96 | (62) | EAEAYKAYKAAAAAA | 6 | >1000 | 43 |
|  | 99 | (63) | EAAAYKAYKAAAAAA | 5 | >150 | 57 |
|  | 100 | (64) | EAAKYEAYKAAAAAA | >150 | 2 | 56 |
|  | 101 | (65) | EKAKYEAYKAAAAAA | 3 | <1 | 53 |
|  | 102 | (66) | EAKKYEAYKAAAAAA | 20 | 2 | 57 |
|  | 103 | (67) | AKKEYAEYKAAAAAA | >150 | <1 | 49 |
|  | 104 | (68) | AAEKYAEYKAAAAAA | >150 | 20 | 53 |
| 5. | 107 | (69) | ENPVVHYFKNIVTPR | <1 | 40 | 64 |
|  | 106 | (70) | EEKAYAYAKAAAAAA | >1000 | 100 | 39 |
|  | 108 | (71) | EEAAYKAAKAAAAAA | >1000 | 2 | 23 |
|  | 109 | (72) | EEKAYAAAKAAAAAA | >1000 | 3 | 12 |
|  | 110 | (73) | EEKAYAAAKAAAAAA | >1000 | 20 | 16 |
|  | 111 | (74) | EEAAYKAAKAAAAAA | >1000 | <1 | 21 |
|  | 112 | (75) | EEAAYAYKKAAAAAA | >1000 | 15 | 32 |
|  | 113 | (76) | EAKAYEYAKAAAAAA | >1000 | <1 | 30 |
| 6. | 114 | (77) | AAEKVAAAAAAAAAA | >1000 | >1000 | 34 |
|  | 115 | (78) | AAAKYAAAAAAAAAA | >1000 | >1000 | 25 |
|  | 116 | (79) | AAAKVAAAAAAAAAA | >1000 | >1000 | 30 |
|  | 117 | (80) | AAEAYAAAAAAAAAA | >1000 | >1000 | 25 |
|  | 118 | (81) | AAEAVAAAAAAAAAA | >1000 | >1000 | 38 |
|  | 119 | (82) | AAEKAAAAAAAAAAA | >1000 | >1000 | 26 |

[a]Peptide number in the peptide set given as #. The SEQ ID NO is in parenthesis. The P1 position amino acid residue in each sequence is shown in bold.
[b]IC$_{50}$ values were calculated from the competitive binding assays with the biotinylated MBP 85-99 (0.13 µM) or Cop 1 (average MW 8,150) (1.5 µM) in a final volume of 50 µl and various concentrations of the unlabeled peptides, as described in Materials and Methods. Results represent one out of two independent experiments.
[c]Values represent inhibition of IL-2 production by IL-2-dependent CTLL in response to supernatants taken from incubations in duplicates of the MGAR cells with MBP 85-99 (final peptide concentration 12.5 µM) plus the synthetic peptides or Cop 1 (20.8 µM each), and MBP 84-102-specific HLA-DR2-36estricted T cell transfectant Hy1B (patient Hy, DRB1*1602). The background counts with no antigen (9,000-11,000 cpm) were subtracted from the experimental-36-data. Proliferation in response to MBP 85-99 alone was 49,625 cpm. For experimental details see Materials and Methods.
[d]NA, not applicable.

What is claimed is:

1. A composition comprising a synthetic peptide having an amino acid sequence selected from the group consisting of:

| | |
|---|---|
| AAEAYKAYKAAAAAA, | (SEQ ID NO: 60) |
| EAAAYKAYKAAAAAA, | (SEQ ID NO: 63) |
| AKKEYAEYKAAAAAA, | (SEQ ID NO: 67) |
| EAPAYKAYKAAAAPA, | (SEQ ID NO: 83) |
| EKPKYEAYKAAAAPA, | (SEQ ID NO: 85) |
| AKPEYAEYKAAAAPA, | (SEQ ID NO: 87) |
| EAPKFEAYKAAAAPA, and | (SEQ ID NO: 98), |
| EAPKVEAYKAAAAPA | (SEQ ID NO: 99) | further comprising substitution of a tyrosine (Y) in the P1 position of the peptide by a valine (V) in those sequences having a tyrosine in the P1 position.

2. A composition comprising a synthetic peptide having an amino acid sequence selected from the group consisting of:
AAEAYKAYKAAAAAA (SEQ ID NO: 60),
EAAAYKAYKAAAAAA (SEQ ID NO: 63),
EAAKYEAYKAAAAAA (SEQ ID NO: 64),
EKAKYEAYKAAAAAA (SEQ ID NO: 65),
EAKKYEAYKAAAAAA (SEQ ID NO: 66),
AKKEYAEYKAAAAAA (SEQ ID NO: 67),
EAPAYKAYKAAAAPA (SEQ ID NO: 83),
EAPKYEAYKAAAAPA (SEQ ID NO: 84),
EKPKYEAYKAAAAPA (SEQ ID NO: 85),
EAPKYEAYKAAAAPA (SEQ ID NO: 86),
AKPEYAEYKAAAAPA (SEQ ID NO: 87),
APEKAKYEAYKAAAAAA (SEQ ID NO: 88),
APEKAKYEAYKAAAAAPA (SEQ ID NO: 89),
EKAKYEAYKAAAAAPA (SEQ ID NO: 90),
EKPKFEAYKAAAAPA (SEQ ID NO: 91),
EKPKVEAYKAAAAPA (SEQ ID NO: 93),
EKAKFEAFKAAAAAA (SEQ ID NO: 95),
APEKAKFEAFKAAAAPA (SEQ ID NO: 96),
APEKAKFEAYKAAAAPA (SEQ ID NO: 97),
EAPKFEAYKAAAAPA (SEQ ID NO: 98), and
EAPKVEAYKAAAAPA (SEQ ID NO: 99),
further comprising substitution of a tyrosine (Y) in the P1 position by a valine (V).

3. A kit comprising at least one container having a peptide as shown in claim 1, in a pharmaceutically acceptable buffer, and instructions for use.

4. A kit comprising at least one container having a peptide as shown in claim 2, in a pharmaceutically acceptable buffer, and instructions for use.

* * * * *

UNITED STATES PATENT AND TRADEMARK OFFICE
CERTIFICATE OF CORRECTION

PATENT NO. : 7,456,252 B2
APPLICATION NO. : 11/150755
DATED : November 25, 2008
INVENTOR(S) : Strominger et al.

Page 1 of 1

It is certified that error appears in the above-identified patent and that said Letters Patent is hereby corrected as shown below:

In the Specification

Column 1, Lines 17-19, delete, "This invention was made in part with government Support under grant CA-47554 awarded by the National Institutes of Health. The government has certain rights in the invention." and insert -- This invention was made with government support under CA047554 and AI049524 awarded by the National Institutes of Health. The government has certain rights in the invention. --

Signed and Sealed this
Fourth Day of August, 2020

Andrei Iancu
*Director of the United States Patent and Trademark Office*